(12) United States Patent  
Bejarano et al.

(10) Patent No.: US 12,263,111 B2
(45) Date of Patent: Apr. 1, 2025

(54) BRACE LIMITING RANGE OF MOTION AND METHOD OF USING SAME

(71) Applicant: DJO, LLC, Carlsbad, CA (US)

(72) Inventors: Robert Bejarano, Carlsbad, CA (US); Edward Maher, Oceanside, CA (US)

(73) Assignee: DJO, LLC, Carlsbad, CA (US)

( * ) Notice: Subject to any disclaimer, the term of this patent is extended or adjusted under 35 U.S.C. 154(b) by 0 days.

(21) Appl. No.: 18/519,752

(22) Filed: Nov. 27, 2023

(65) Prior Publication Data

US 2024/0099872 A1 Mar. 28, 2024

Related U.S. Application Data

(63) Continuation of application No. 16/714,119, filed on Dec. 13, 2019, now abandoned.

(Continued)

(51) Int. Cl.
*A61F 5/01* (2006.01)

(52) U.S. Cl.
CPC .... *A61F 5/0125* (2013.01); *A61F 2005/0158* (2013.01); *A61F 2005/0165* (2013.01)

(58) Field of Classification Search
CPC .... A61F 5/00; A61F 5/05; A61F 5/013; A61F 5/0102; A61F 5/0123; A61F 5/0125; A61F 2005/0132; A61F 2005/0137; A61F 2005/0139; A61F 2005/0146; A61F 2005/0155; A61F 2005/0158; A61F 2005/0165; A61F 2005/0167; A61F 2005/0169; A61F 2005/0174; A61F 2005/0175; A61F 2005/0179; A61F 2005/0181; A61F 2005/0197; A42B 3/185; A44B 11/06

See application file for complete search history.

(56) References Cited

U.S. PATENT DOCUMENTS 4,791,916 A  12/1988 Paez
5,063,916 A  11/1991 France et al.
(Continued)

FOREIGN PATENT DOCUMENTS

CN  102574285 A  7/2012
CN  203777120 U  8/2014
(Continued)

OTHER PUBLICATIONS

Notice of acceptance for patent application Received for AU Application Serial No. 2019401444 dated Nov. 7, 2022, 03 pages.
(Continued)

*Primary Examiner* — Ophelia A Hawthorne
*Assistant Examiner* — Gina Mccarthy
(74) *Attorney, Agent, or Firm* — Veros Legal Solutions, LLP

(57) ABSTRACT

A brace is provided including an upper support arm, a lower support arm, a hinge assembly configured to rotatably couple the upper support arm to the lower support arm, a plurality of cuffs, each coupled directly or indirectly to the upper support arm or the lower support arm and configured to receive a respective strap for securing the brace to an appendage of the subject, and a plurality of buckles, each configured to be coupled to a respective one of the plurality of cuffs and to receive one of the respective straps.

16 Claims, 16 Drawing Sheets

Related U.S. Application Data

(60) Provisional application No. 62/782,707, filed on Dec. 20, 2018.

(56) References Cited

U.S. PATENT DOCUMENTS

| | | | |
|---|---|---|---|
| 5,328,446 A | 7/1994 | Bunnell et al. |
| 5,460,599 A | 10/1995 | Davis et al. |
| 5,586,970 A | 12/1996 | Morris et al. |
| 5,672,152 A | 9/1997 | Mason et al. |
| 5,772,618 A | 6/1998 | Mason et al. |
| 5,807,294 A | 9/1998 | Cawley et al. |
| 5,827,208 A | 10/1998 | Mason et al. |
| 5,938,629 A | 8/1999 | Bloedau |
| 6,203,511 B1 | 3/2001 | Johnson et al. |
| 6,325,773 B1 | 12/2001 | Opel |
| 6,375,632 B1 | 4/2002 | Albrecht et al. |
| 6,402,711 B1 | 6/2002 | Nauert |
| 6,666,837 B2 | 12/2003 | Weihermüller |
| 6,689,080 B2 | 2/2004 | Castillo |
| 6,719,713 B2 | 4/2004 | Mason |
| 6,740,054 B2 | 5/2004 | Stearns |
| 6,793,641 B2 | 9/2004 | Freeman et al. |
| 6,845,548 B1 * | 1/2005 | Lin ..................... A42B 3/185 24/324 |
| 6,913,587 B2 | 7/2005 | Slishman |
| 6,936,019 B2 | 8/2005 | Mason |
| 6,942,629 B2 | 9/2005 | Hepburn et al. |
| 7,011,640 B2 | 3/2006 | Patterson et al. |
| 7,037,287 B2 | 5/2006 | Cormier et al. |
| 7,059,329 B2 | 6/2006 | Mason et al. |
| 7,083,583 B2 | 8/2006 | Opahle et al. |
| 7,117,569 B2 | 10/2006 | Bledsoe |
| 7,201,728 B2 | 4/2007 | Sterling |
| 7,235,059 B2 | 6/2007 | Mason et al. |
| 7,435,234 B2 | 10/2008 | Gamada |
| 7,479,122 B2 | 1/2009 | Ceriani et al. |
| 7,485,103 B2 | 2/2009 | Mason et al. |
| 7,500,957 B2 | 3/2009 | Bledsoe |
| 7,513,881 B1 | 4/2009 | Grim et al. |
| 7,524,296 B2 | 4/2009 | Patterson et al. |
| 7,534,219 B2 | 5/2009 | Stearns |
| 7,534,220 B2 | 5/2009 | Cormier et al. |
| 7,662,119 B2 | 2/2010 | Detoro et al. |
| 7,806,842 B2 | 10/2010 | Stevenson et al. |
| 7,841,999 B2 | 11/2010 | Napholz |
| 7,887,496 B2 | 2/2011 | Kahlmeyer et al. |
| 7,984,531 B2 | 7/2011 | Moore |
| 7,988,652 B2 | 8/2011 | Chao |
| 8,048,013 B2 | 11/2011 | Ingimundarson et al. |
| 8,128,587 B2 | 3/2012 | Stevenson et al. |
| 8,167,829 B2 | 5/2012 | Sterling et al. |
| 8,172,781 B2 | 5/2012 | Oddou et al. |
| 8,273,045 B2 | 9/2012 | Ceriani |
| 8,277,403 B2 | 10/2012 | Ceriani et al. |
| 8,348,876 B2 | 1/2013 | Ingimundarson et al. |
| 8,419,670 B2 | 4/2013 | Downing |
| 8,728,018 B2 | 5/2014 | McCune |
| 8,740,829 B2 | 6/2014 | Lee et al. |
| 8,945,031 B2 | 2/2015 | Cardinali |
| 9,039,644 B2 | 5/2015 | Ingimundarson et al. |
| 9,125,730 B2 | 9/2015 | Ingimundarson et al. |
| 9,132,026 B2 | 9/2015 | Bledsoe et al. |
| 9,220,624 B2 | 12/2015 | Jansson et al. |
| 9,345,607 B2 | 5/2016 | Lee et al. |
| 9,351,864 B2 | 5/2016 | Romo et al. |
| 9,398,971 B2 | 7/2016 | Chiang et al. |
| 9,510,967 B2 | 12/2016 | Lee et al. |
| 9,539,135 B2 | 1/2017 | Romo et al. |
| 9,615,955 B2 | 4/2017 | Bledsoe |
| 9,668,903 B2 | 6/2017 | Hsu et al. |
| 9,724,226 B2 | 8/2017 | Hollister et al. |
| 2006/0155229 A1 * | 7/2006 | Ceriani ................. A61F 5/0125 602/5 |
| 2006/0155230 A1 | 7/2006 | Mason et al. |
| 2006/0265845 A1 * | 11/2006 | Saderholm ............. A44B 11/06 24/595.1 |
| 2013/0178772 A1 | 7/2013 | Oaks et al. |
| 2013/0269628 A1 * | 10/2013 | Holt, Jr. ............... A01K 27/001 119/863 |
| 2014/0207038 A1 | 7/2014 | Santaniello et al. |
| 2015/0018735 A1 * | 1/2015 | Chetlapalli ........... A61F 5/0123 602/16 |
| 2015/0141888 A1 | 5/2015 | Chiang et al. |
| 2015/0374531 A1 | 12/2015 | Fedon |
| 2015/0374532 A1 | 12/2015 | Fedon |
| 2017/0281389 A1 | 10/2017 | Frost et al. |
| 2020/0197209 A1 | 6/2020 | Bejarano et al. |

FOREIGN PATENT DOCUMENTS

| | | |
|---|---|---|
| CN | 104203165 A | 12/2014 |
| CN | 108135720 A | 6/2018 |
| EP | 1829507 A1 | 9/2007 |
| EP | 2585008 A1 | 5/2013 |
| EP | 3037075 A2 | 6/2016 |
| GB | 9506224 | 5/1995 |
| WO | 2020131636 A2 | 6/2020 |

OTHER PUBLICATIONS

Partial European Search Report mailed Feb. 12, 2024 in 23188659.9.

PCT/US2019/066334—International Search Report—Mailed Jun. 25, 2020.

* cited by examiner

BRACE LIMITING RANGE OF MOTION AND METHOD OF USING SAME

CROSS-REFERENCE TO RELATED APPLICATIONS

This application is a continuation of pending U.S. Non-Provisional application Ser. No. 16/714,119 filed, on Dec. 13, 2019, which claims priority to U.S. Provisional Application No. 62/782,707, filed on Dec. 20, 2018, the entire contents of all of which are hereby incorporated by reference.

BACKGROUND

Field of the Disclosure

The present disclosure relates generally to a brace configured to limit a range of motion of a joint of a user and a method of using the same.

Description of the Related Technology

Damaged ligaments, cartilage, and tendons in joints are not an uncommon occurrence, particularly with today's emphasis on physical activity and conditioning. Few injuries interfere with motion more than injuries to the knee. Knee injuries account for approximately 60% of all sports related injuries with nearly half of those injuries occurring to the ACL. ACL injury is most prevalent (1 in 1,750 persons) in patients between the ages of 15 and 45, due in no small measure to their more active lifestyle as well as higher participation in sports. A person who has torn their ACL has a 15 times greater risk of a second ACL injury during the initial 2 months after ACL reconstruction, and risk of ACL injury to the opposite knee is two times that of the restructured knee.

There are four main ligaments which hold the knee together: Anterior Cruciate Ligament (ACL), Posterior Cruciate Ligament (PCL), Medial Collateral Ligament (MCL) and Lateral Collateral Ligament (LCL). There are over 200,000 ACL injuries that occur in the United States annually. Approximately 50% of ACL injuries occur with injuries to other structures of the knee. While less common than an ACL injury, injuries to the PCL account for between 3% to 20% of all knee ligament injuries. The collateral ligaments, MCL and LCL, are responsible for 25% of knee injuries in competitive athletes.

Treatments for ACL and other ligament injuries include surgical and non-surgical options. Braces are employed to limit range of motion, promote support and stabilization while ligaments heal. In the case of ACL surgery, graft strength of a new ACL is considerably weaker than the native ACL during the first 12 months, so a brace configured to limit the range of motion of a joint of the user during this early period helps protect it from harmful forces that occur in everyday life or in sports activity.

SUMMARY

According to some embodiments, a brace configured to restrict a range of motion of a joint of a subject is provided. The brace includes an upper support arm. The brace includes a lower support arm. The brace includes a hinge assembly. The hinge assembly includes an upper hinge plate coupled to the upper support arm and comprising a first plurality of teeth disposed along at least a portion of a perimeter of the upper hinge plate. The hinge assembly includes a lower hinge plate coupled to the lower support arm and comprising a second plurality of teeth disposed along at least a portion of a perimeter of the upper hinge plate. The hinge assembly includes an axle rotatably coupling the upper hinge plate and the lower hinge plate. The hinge assembly includes a locking element disposed on the upper hinge plate. The locking element includes a first protrusion and a second protrusion configured to physically contact opposite sides of one of the second plurality of teeth in a first orientation, thereby prohibiting rotation of the upper support arm with respect to the lower support arm.

According to some embodiments, a method of restricting a range of motion of a joint of a subject utilizing a brace configured for attachment to the joint is provided. The method includes securing an upper support arm of the brace against an upper portion of an appendage of the subject. The method includes securing a lower support arm of the brace against a lower portion of the appendage. The method includes restricting a range of motion of the upper support arm with respect to the lower support arm utilizing a hinge assembly of the brace. The hinge assembly includes an upper hinge plate coupled to the upper support arm and comprising a first plurality of teeth disposed along at least a portion of a perimeter of the upper hinge plate. The hinge assembly includes a lower hinge plate coupled to the lower support arm and comprising a second plurality of teeth disposed along at least a portion of a perimeter of the upper hinge plate. The hinge assembly includes an axle rotatably coupling the upper hinge plate and the lower hinge plate. The hinge assembly includes a locking element disposed on the upper hinge plate, the locking element comprising a first protrusion and a second protrusion configured to physically contact opposite sides of one of the second plurality of teeth in a first orientation, thereby prohibiting rotation of the upper support arm with respect to the lower support arm.

According to some embodiments, a method of manufacturing a brace configured to restrict a range of motion of a joint of a subject is provided. The method includes providing an upper support arm. The method includes providing a lower support arm. The method includes assembling a hinge assembly. Assembling the hinge assembly includes coupling an upper hinge plate to the upper support arm, the upper hinge plate comprising a first plurality of teeth disposed along at least a portion of a perimeter of the upper hinge plate. Assembling the hinge assembly includes coupling a lower hinge plate to the lower support arm, the lower hinge plate comprising a second plurality of teeth disposed along at least a portion of a perimeter of the upper hinge plate. Assembling the hinge assembly includes rotatably coupling the upper hinge plate and the lower hinge plate via an axle. Assembling the hinge assembly includes disposing a locking element on the upper hinge plate. The locking element includes a first protrusion and a second protrusion configured to physically contact opposite sides of one of the second plurality of teeth in a first orientation, thereby prohibiting rotation of the upper support arm with respect to the lower support arm.

DETAILED DESCRIPTION

Figure 1:
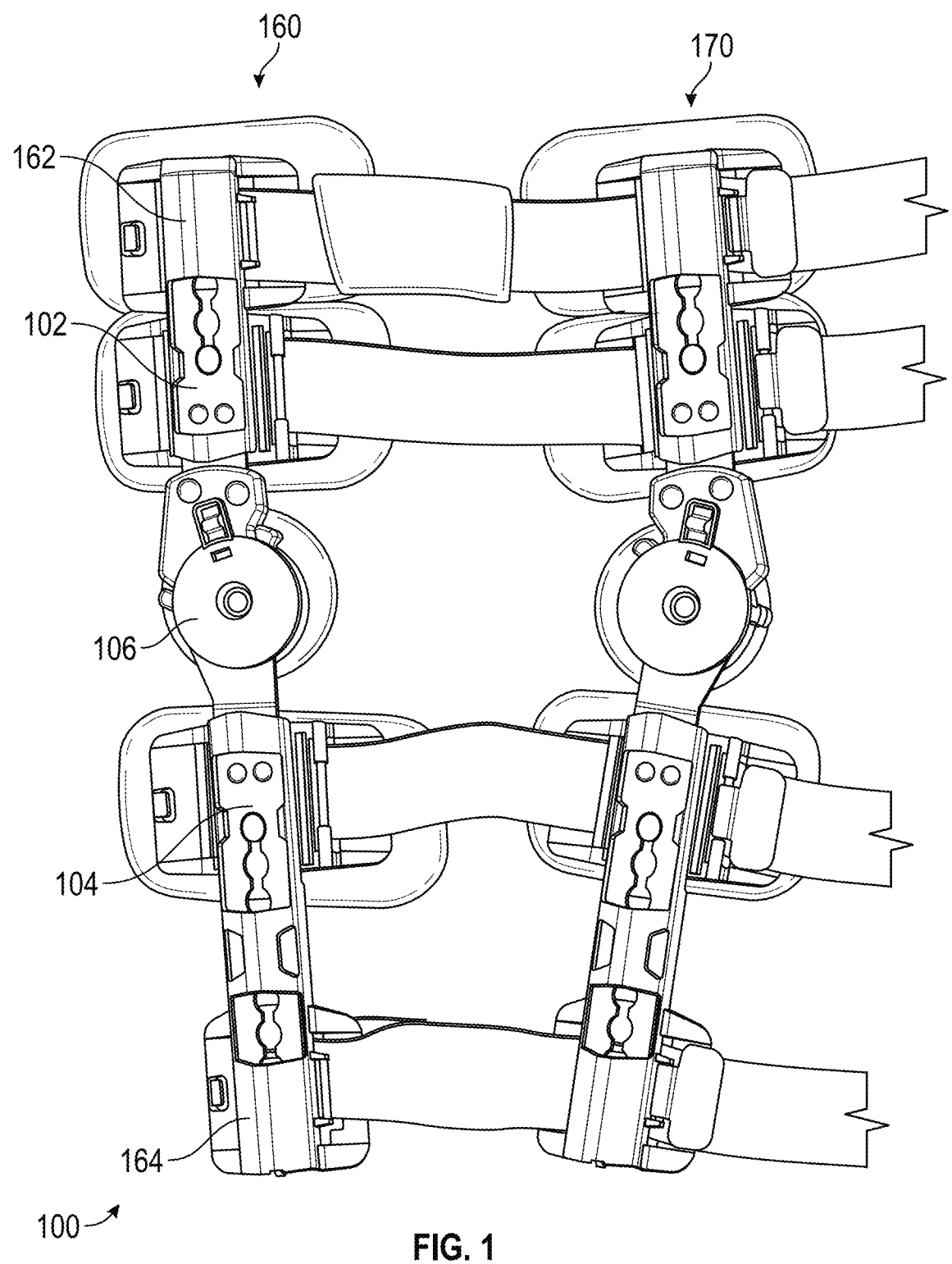
FIG. 1 illustrates a brace configured for attachment to a joint of a user, in accordance with some embodiments.

Embodiments of this disclosure relate to orthopedic braces for use in treating a variety of injuries to the knee, or other joint, and surrounding ligaments. More particularly, embodiments of the brace disclosed herein may be intended for use in post-operative activities and/or activities of daily living for patients with ACL deficiencies, collateral ligament deficiencies, hyperextension injury, or for prophylactic use.

Orthotic bracing and support can promote healing and wellness through the benefit of natural motion through safe ranges of motion (ROM) and/or by locking a joint in a desired orientation. Post-surgical recovery of the patient may be at least partially dependent upon locking the affected joint in a desired orientation and/or limiting ROM to a predetermined safe range. Accordingly, there is a need for bracing solutions configured to lock the affected joint in a desired orientation and/or limit ROM to a predetermined safe range.

A better understanding of the various features of the disclosure can be gleaned from the following description read in conjunction with the accompanying drawings in which like reference characters refer to like elements, where reasonably applicable. While the disclosure may be susceptible to various modifications and alternative constructions, certain illustrative features are shown in the drawings and are described in detail below. It will be understood, however, that there is no intention to limit the disclosure to the specific embodiments disclosed, but to the contrary, the intention is to cover all modifications, alternative constructions, combinations, and equivalents falling within the spirit and scope of the disclosure.

Furthermore, it will be appreciated that unless a term is expressly defined in this disclosure to possess a described meaning, there is no intent to limit the meaning of such term, either expressly or indirectly, beyond its plain or ordinary meaning.

For ease of understanding the disclosed features of an orthopedic device, as used herein, "proximal" has its ordinary meaning and refers to a location situated next to or near the point of attachment or origin or a central point or located toward the center of the body. Likewise, the term "distal" has its ordinary meaning and refers to a location that is situated away from the point of attachment or origin or central point or located away from the center of the body. The term "medial" refers to a position that is closer to the midline of the body, whereas the term "lateral" refers to a position further from the midline of the body. The terms "upper" and "lower" describe the position of certain elements as being either above or below a hinge assembly of the brace. An "upper" element is above the hinge assembly and knee or other joint, whereas a "lower" element is below the hinges assembly and knee or other joint. The term "posterior" also has its ordinary meaning and refers to a location that is behind or to the rear of another location or feature. Lastly, the term "anterior" has its ordinary meaning and refers to a location that is ahead of or to the front of another location or feature.

The terms "rigid," "flexible," "malleable" and "resilient" may be used herein to distinguish portions of certain features of the orthopedic device. The term "rigid" is intended to mean an element of the device is generally or substantially inflexible. Within the context of frame or support members or shells that are "rigid," it is intended to indicate that they do not lose their overall shape when force is applied. The term "flexible" or "malleable", by contrast, is intended to encompass features that are capable of bending or flexing under load.

FIG. 1 illustrates a brace 100 configured for attachment to a joint of a user, in accordance with some embodiments. Brace 100 includes at least one of lateral portion 160 configured to abut a lateral side of an appendage of a user, and a medial portion 170 configured to abut a medial side of the appendage of the user. As will be described in more detail in connection with the following figures, lateral and medial portions 160, 170 may each comprise an upper support arm 102, a lower support arm 104, and a hinge assembly 106 configured to rotatably couple upper support arm 102 to lower support arm 104. Hinge assembly 106 is further configured to limit a range of motion of upper support arm 102 with respect to lower support arm 104 in at least one of a first rotational direction and a second rotational direction. As will be described in more detail below, each of lateral and medial portions 160, 170 may further comprise an upper slider 162 configured to slidably couple to upper support arm 102 and a lower slider 164 configured to slidably couple to lower support arm 104. Brace 100 may be secured to an appendage of a user utilizing one or more straps configured to secure upper and lower support arms 102, 104 and upper and lower sliders 162, 164 against a side of a user's appendage. Various features, aspects and elements of brace 100 will now be described in more detail in connection with the following figures.

Figure 2A:
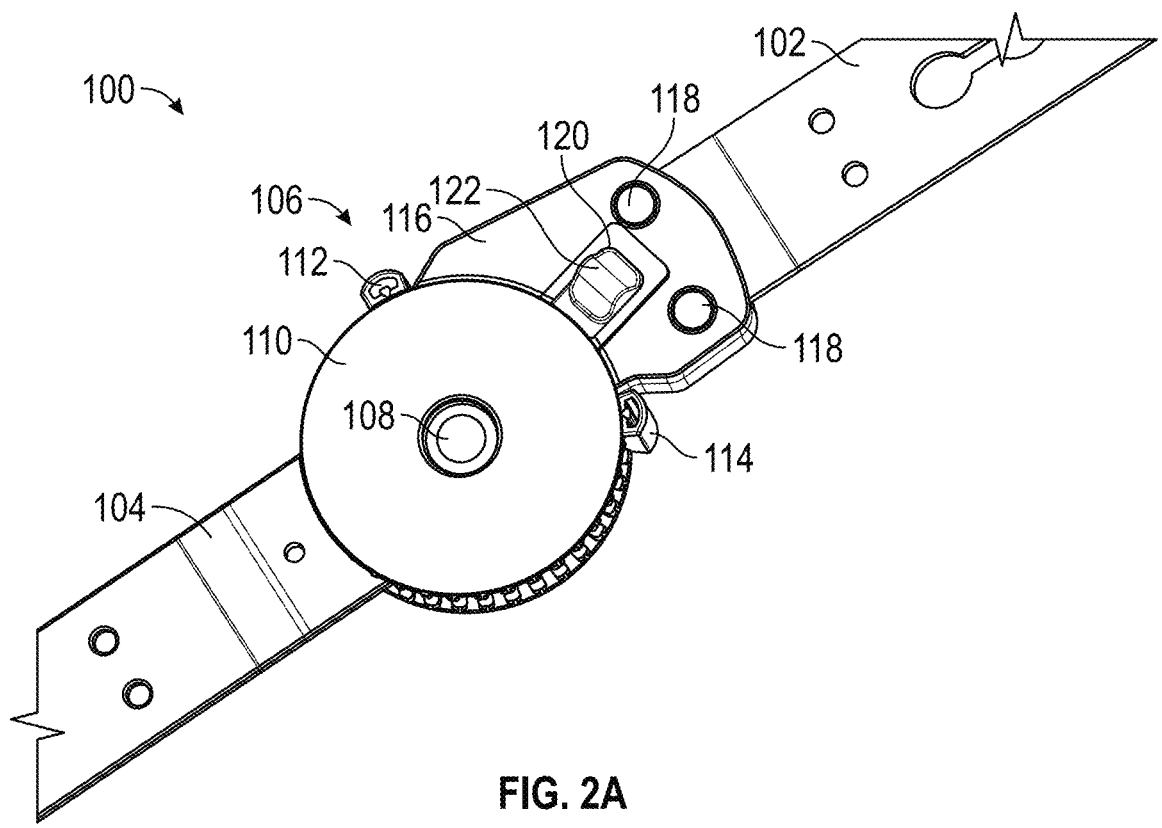
FIG. 2A illustrates a hinge assembly of the brace of FIG. 1, in accordance with some embodiments.
Figure 2B:
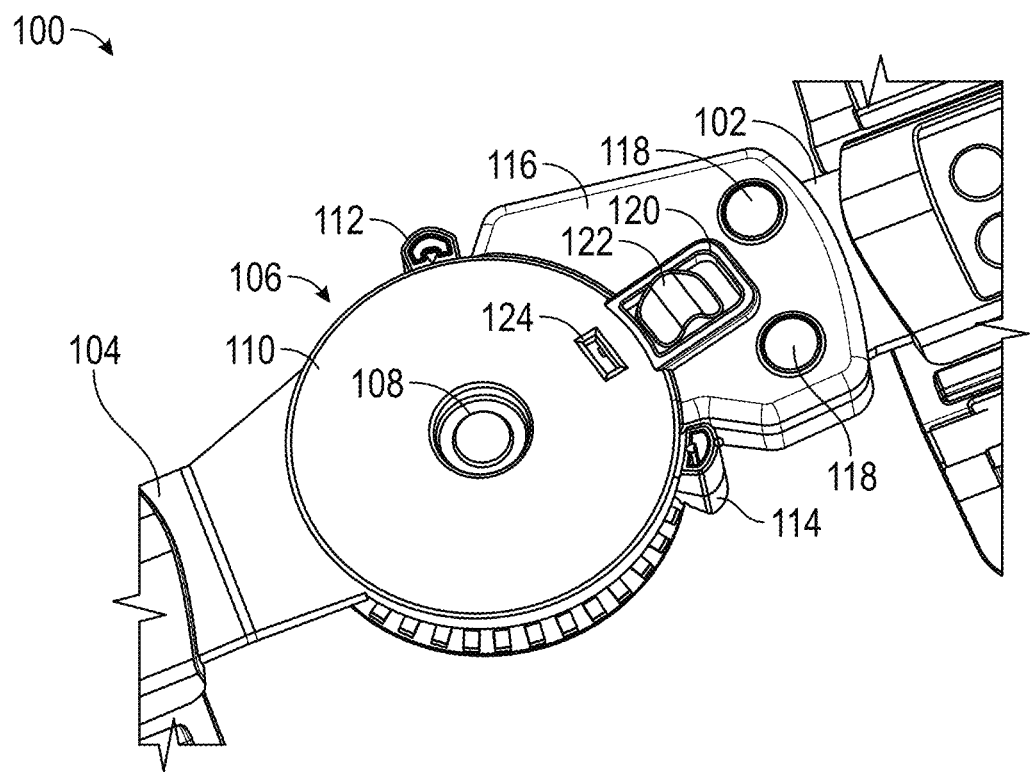
FIG. 2B illustrates the hinge assembly FIG. 2A further comprising a window configured to provide visual indication of a locked state of the hinge assembly, in accordance with some embodiments.

FIG. 2A illustrates hinge assembly 106 of brace 100 of FIG. 1, in accordance with some embodiments, while FIG. 2B illustrates hinge assembly 106 of FIG. 2A further comprising a window 124 configured to provide visual indication of a locked state of hinge assembly 106, in accordance with some embodiments. Discussion of hinge assembly 106 will be described in connection with FIGS. 2A and 2B together below.

The terms "hinge" or "hinge assembly" as used herein means a mechanical coupler that ties two arms of the brace together while allowing rotational motion through different angular orientations of the longitudinal axes of the two arms. For example, as shown in FIGS. 2A and 2B, hinge assembly 106 mechanically couples upper support arm 102 and lower support arm 104 about an axle 108. Upper and lower support arms 102, 104 may comprise any suitably rigid material, e.g., metal, plastic, fiberglass composite, etc.

Hinge assembly 106 comprises a hinge cover 110 configured to cover at least some internal components of hinge assembly 106 as will be described in more detail below. When in use, hinge assembly 106 is generally proximate to the anatomical joint being braced, for example and not limitation, a knee or an elbow joint. Hinge assembly 106 comprises a first range of motion stop 112 configured to limit a range of motion of upper support arm 102 with respect to lower support arm 104 in a first rotational direction. Hinge assembly 106 may further comprise a second range of motion stop 114 configured to limit a range of motion of upper support arm 102 with respect to lower support arm 104 in a second rotational direction opposite the first rotational direction. In some embodiments, first and second range of motion stops 112, 114 may comprise any suitably resilient material, e.g., plastic, which in some cases may be injection molded.

Hinge assembly 106 comprises an outer housing 116 configured to enclose at least some internal components of hinge assembly 106 as will be described in more detail below. Outer housing 116 comprises one or more fasteners 118 configured to secure outer housing 116 to hinge assembly 106. In some embodiments, fasteners 118 may be rivets, screws, or any other suitable fastening element(s). Outer housing 116 further comprises an aperture 120 within which a hinge lock 122 is configured to slide. Hinge lock 122 is configured to lock hinge assembly 106 in a desired orientation about axle 108 when the hinge lock 122 is positioned in a first orientation (e.g., a locked orientation). The hinge lock 122 is configured to allow hinge assembly 106 to move freely about axle 108 within the range of motion set by first and second range of motion stops 112, 114 when hinge lock 122 is positioned in a second orientation (e.g., an unlocked orientation). In some embodiments, hinge lock 122 may comprise a slider, a button, or any other suitable element configured to slide, toggle, or shift between the first orientation and the second orientation within aperture 120. In some embodiments, the first orientation may be more proximal to axle 108, within aperture 120, compared to the second orientation.

In some embodiments, as shown in FIG. 2B, hinge cover 110 comprises window 124 configured to provide visual indication of a locked state of hinge assembly 106. For example, a portion of hinge lock 122 may be visible through window 124 when hinge lock 122 is in the first orientation, thereby indicating hinge assembly 106 is in a locked state. In such embodiments, the same portion of hinge lock 122, visible through window 124 when hinge lock 122 is in the first orientation, is not visible through window 124 when hinge lock 122 is in the second orientation, thereby indicating hinge assembly 106 is not in the locked state. In some embodiments, at least the portion of hinge lock 122, visible through window 124 when hinge lock 122 is in the first orientation, has an easily noticeable color, e.g., red or orange, or other pattern, thereby providing an easily noticeable indication to a user when hinge assembly 106 is in a locked state.

Figure 3A:
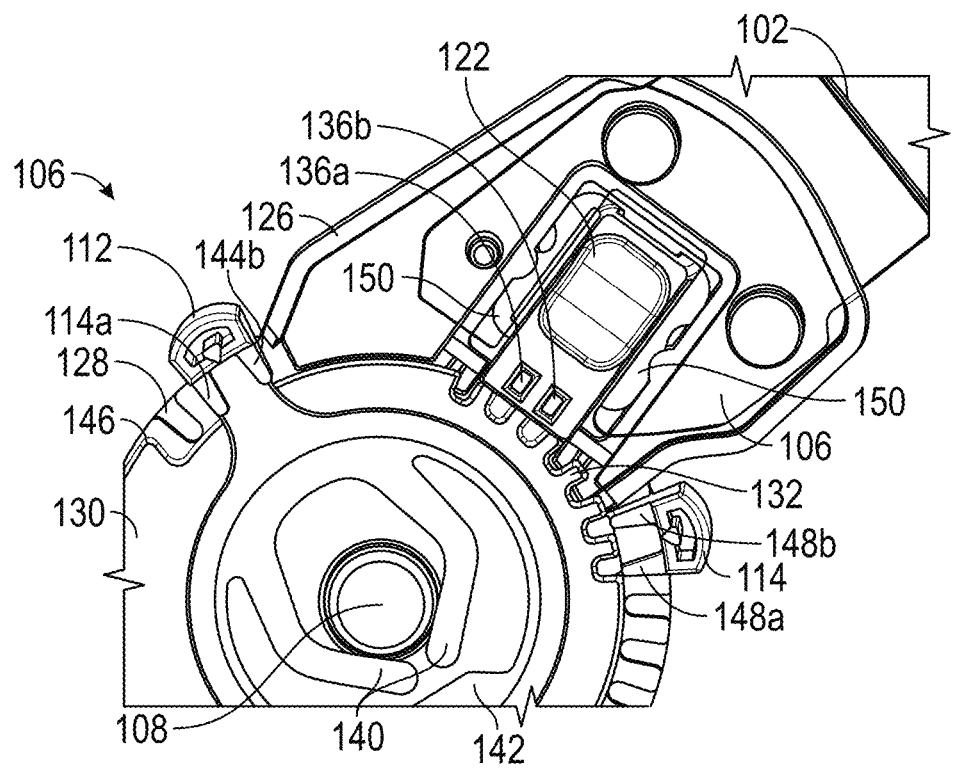
FIG. 3A illustrates a plan view of a hinge assembly of the brace of FIG. 1 in an unlocked configuration, in accordance with some embodiments.
Figure 3B:
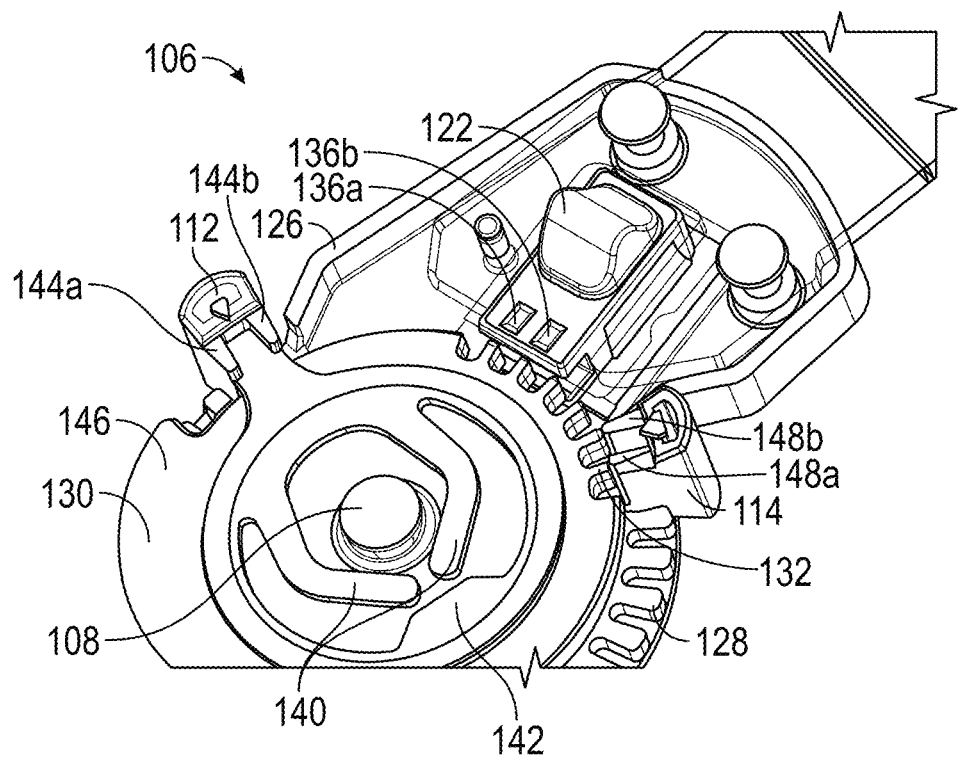
FIG. 3B illustrates a perspective view of the hinge assembly of FIG. 3A in the unlocked configuration.
Figure 4A:
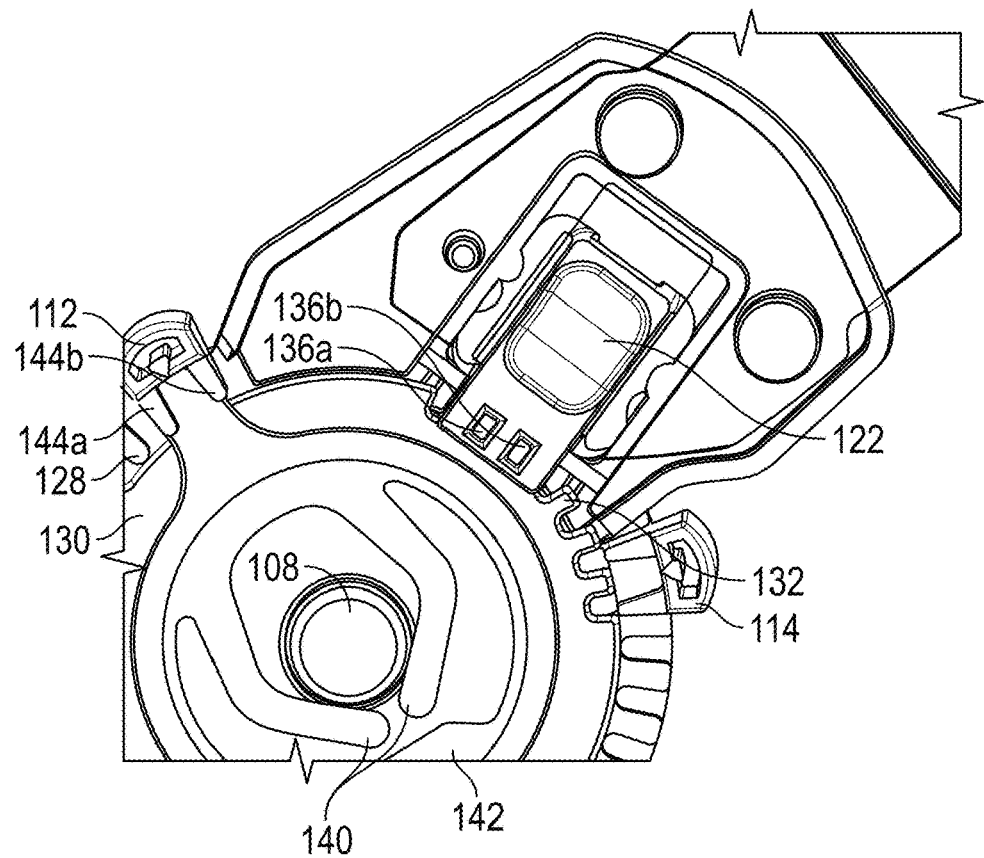
FIG. 4A illustrates a plan view of a hinge assembly of the brace of FIG. 1 in a locked configuration, in accordance with some embodiments.
Figure 4B:
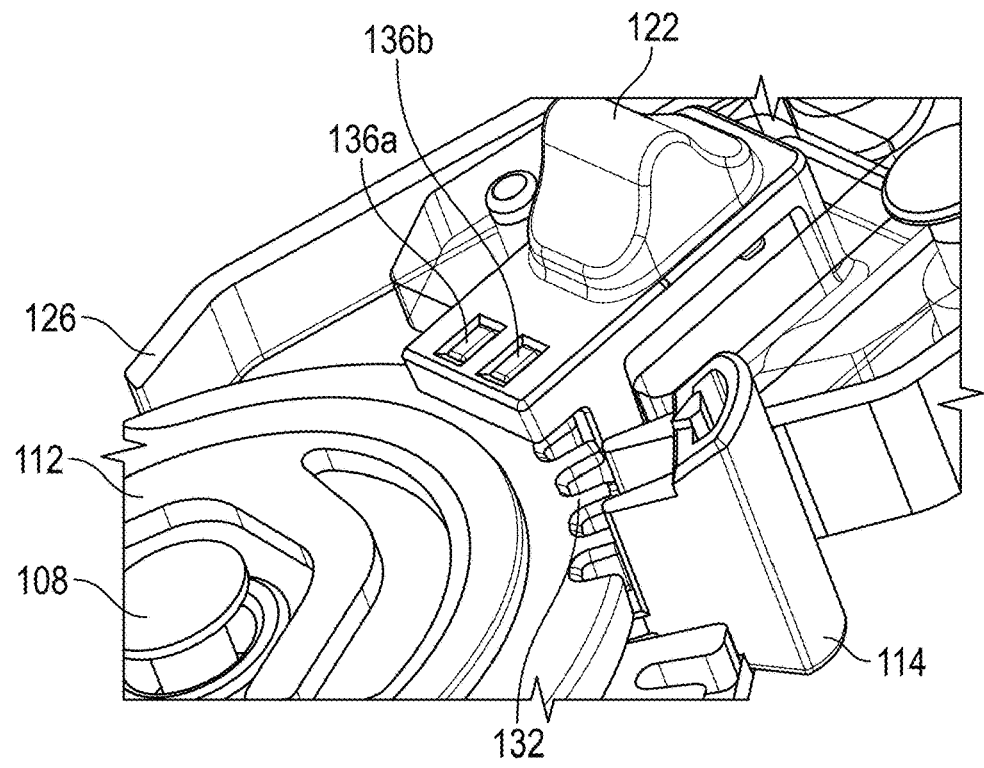
FIG. 4B illustrates a perspective view of the hinge assembly of FIG. 4A in the locked configuration, in accordance with some embodiments.

FIG. 3A illustrates a plan view of hinge assembly 106 of the brace of FIG. 1 in an unlocked configuration, in accordance with some embodiments, while FIG. 3B illustrates a perspective view of hinge assembly 106 of FIG. 3A in the unlocked configuration. FIG. 4A illustrates a plan view of hinge assembly 106 of the brace of FIG. 1 in a locked configuration, in accordance with some embodiments, while FIG. 4B illustrates a perspective view of hinge assembly 106 of FIG. 4A in the locked configuration. FIGS. 3A-4B illustrate hinge assembly 106 with hinge cover 110 and outer housing 116 removed for easy viewing of components located thereunder.

Hinge assembly 106 comprises an upper hinge plate 126 coupled to upper support arm 102 utilizing any suitable coupling element(s), for example rivets, screws or welds. At least a portion of upper hinge plate 126 has a substantially circular perimeter centered about axle 108. At least a portion of the substantially circular perimeter comprises a plurality of teeth 128. In some embodiments, upper hinge plate 126 and upper support arm 102 may be formed as a single, integral component.

Hinge assembly 106 comprises a lower hinge plate 130 coupled to lower support arm 104 utilizing any suitable coupling element(s), for example rivets, screws or welds. At least a portion of lower hinge plate 130 has a substantially circular perimeter centered about axle 108. At least a portion of the substantially circular perimeter comprises a plurality of teeth 132. In some embodiments, lower hinge plate 130 and lower support arm 104 may be formed as a single, integral component. Upper and lower hinge plates 126, 130 may comprise any suitably rigid material, e.g., metal, plastic, fiberglass composite, etc.

In the embodiment of FIGS. 3A and 3B, the hinge lock 122 comprises a body in the form of an open frame with a top panel, a partially open bottom panel, and legs extending therebetween, which may be made of a plastic material. The partially open bottom panel is defined by feet 150 extending between pairs of legs. A first protrusion 136a and a second protrusion 136b are formed by two pins, which may be made of metal. The pins are press fit through aligned openings provided in the top panel and the bottom panel of the hinge lock frame. The centers of the pins are exposed between the top panel and the bottom panel of the hinge lock frame so they can engage teeth 132. In some advantageous embodiments, the location of the hinge lock in the housing is such that allows teeth 132 to be centrally located on the lower hinge plate 130 so the same stamping tool can be used to form both the left and right lower bars.

When locking mechanism 122 is in the second, unlocked orientation as shown in FIGS. 3A and 3B, first and second protrusions 136a, 136b are not in contact with the plurality of teeth 132 of lower hinge plate 130 and upper support arm 102 and lower support arm 104 are free to rotate with respect to one another about axle 108, within a range of motion set by the positions of first and second range of motion stops 112, 114.

However, when locking mechanism 122 is in the first, locked orientation as shown in FIGS. 4A and 4B, first and second protrusions 136a, 136b are configured to physically contact opposite sides of one of the plurality of teeth 132 of lower hinge plate 130, thereby prohibiting rotation of hinge assembly 106 and locking upper support arm 102 with respect to lower support arm 104 in a desired orientation. An orientation of the plurality of teeth 132 of lower hinge plate 130 with respect to hinge lock 122, insert 134 and first and second protrusions 136a, 136b may be such that the same designs for lower hinge plate 130, hinge lock 122, insert 134 and first and second protrusions 136a, 136b may be utilized on any of a lateral or medial side of a joint located on either a left or right side of the user's body. For example, the plurality of teeth 132 may extend radially outward from a point coincident with a center of axle 108 and the first and second orientations of hinge lock 122 may both lie along a straight line extending away from the same point coincident with a center of axle 108. Accordingly, a single design for components of hinge assembly 106 may be utilized on each of the medial and lateral sides of a brace for either a left or a right joint, thereby reducing part count, as well as design and manufacturing costs.

First and second range of motion stops 112, 114 may have substantially similar structure and functionality and will, therefore, now be described together in connection with FIGS. 3A-4B. First range of motion stop 112 is disposed between hinge cover 110 and lower hinge plate 130, while second range of motion stop 114 is disposed between lower hinge plate 130 and upper hinge plate 126.

First range of motion stop 112 comprises a first protrusion 144a and a second protrusion 144b configured to physically contact opposite sides of one of the plurality of teeth 128 of upper hinge plate 126 when first range of motion stop 112 is in a locked position, thereby immobilizing first range of motion stop 112 at a first desired position along the perimeter of upper hinge plate 130. In some embodiments, hinge cover 110 (see FIGS. 2A, 2B) may comprise a plurality of teeth similar to the plurality of teeth 128 of upper hinge plate 126 such that first and second protrusions 144a, 144b also physically contact opposite sides of one of the plurality of teeth of hinge cover 110 when first range of motion stop 112 is in the locked position. Although FIG. 3A does not show the side of first range of motion stop 112 that contacts upper hinge plate 126, first and second protrusions 144a, 144b extend sufficiently toward upper hinge plate 126 to physically contact the plurality of teeth 128 as described above.

First range of motion stop 112 is configured to be pulled in a radial direction with respect to axle 108, such that first and second protrusions 144a, 144b clear the plurality of teeth 128, and then rotated to the first desired position. First range of motion stop 112 comprises a plurality of retention arms 140 configured to contact axle 108 such that, when first range of motion stop 112 is pulled in the radial direction, axle 108 deflects the plurality of retention arms 140 in an outward direction, thereby providing a restoring force that returns first range of motion stop 112 to the locked position when released. In some embodiments, first range of motion stop 112 may also comprise a backstop element 142 configured to contact axle 108 when first range of motion stop 112 is pulled sufficiently far in the radial direction, thereby preventing hyperextension of first range of motion stop 112 or of the plurality of retention arms 140. When in the locked position, first range of motion stop 112 limits the range of motion of upper support arm 102 with respect to lower support arm 104 in a first rotational direction by coming into contact with a first portion 146 of lower hinge plate 130.

First range of motion stop 112, including the plurality of retention arms 140 and backstop element 142, may be integrally molded as a single part, for example, by injection molding. Integrally molding first range of motion stop 112 as a single part eliminates part count and reduces both manufacturing and assembly costs due to labor and/or non-conformity issues that can occur when assembling separate parts. In addition, first range of motion stop 112 may be designed for injection molding such that its molding doesn't require any side action in the tooling. For example, all sides of first range of motion stop 112 may be substantially perpendicular to a plane of first range of motion stop 112, or may slope to one side or the other of perpendicular (but not both at any given point along the sides), so that side molds are not required to allow clearance of stop 112 from its injection mold. This not only reduces tool cost and complexity, it also lowers part cost through faster manufacture cycle time compared to other designs in which side action in the tooling is required to remove a part from its injection mold.

Second range of motion stop 114 comprises a first protrusion 148a and a second protrusion 148b configured to physically contact opposite sides of one of the plurality of teeth 128 of upper hinge plate 126 when second range of motion stop 114 is in a locked position, thereby immobilizing second range of motion stop 114 at a second desired position along the perimeter of upper hinge plate 126. Where hinge cover 110 (see FIGS. 2A, 2B) comprises a plurality of teeth similar to the plurality of teeth 128 of upper hinge plate 126, first and second protrusions 148a, 148b also physically contact opposite sides of one of the plurality of teeth of hinge cover 110 when second range of motion stop 114 is in the locked position. Although FIG. 3A does not show the side of second range of motion stop 114 that contacts upper hinge plate 126, first and second protrusions 148a, 148b extend sufficiently toward upper hinge plate 126 to physically contact the plurality of teeth 128 as described above.

Second range of motion stop 114 is configured to be pulled in a radial direction with respect to axle 108, such that first and second protrusions 148a, 148b clear the plurality of teeth 128, and then rotated to the second desired position. Second range of motion stop 114 comprises a plurality of retention arms (not shown but substantially the same as arms 140) configured to contact axle 108 such that, when second range of motion stop 114 is pulled in the radial direction, axle 108 deflects the plurality of retention arms in an outward direction, thereby providing a restoring force that returns second range of motion stop 114 to the locked position when released. In some embodiments, second range of motion stop 114 may also comprise a backstop element (not shown but substantially the same as backstop element 142) configured to contact axle 108 when second range of motion stop 114 is pulled sufficiently far in the radial direction, thereby preventing hyperextension of second range of motion stop 114 or of the plurality of retention arms 140. When in the locked position, second range of motion stop 114 limits the range of motion of upper support arm 102 with respect to lower support arm 104 in a second rotational direction opposite of the first rotational direction by coming into contact with a second portion (not shown but similar to portion 146) of lower hinge plate 130.

Second range of motion stop 114, including its plurality of retention arms and backstop element may also be integrally molded as a single part, for example, by injection molding and such that its molding doesn't require any side action in the tooling as previously described for first range of motion stop 112.

Figure 5A:
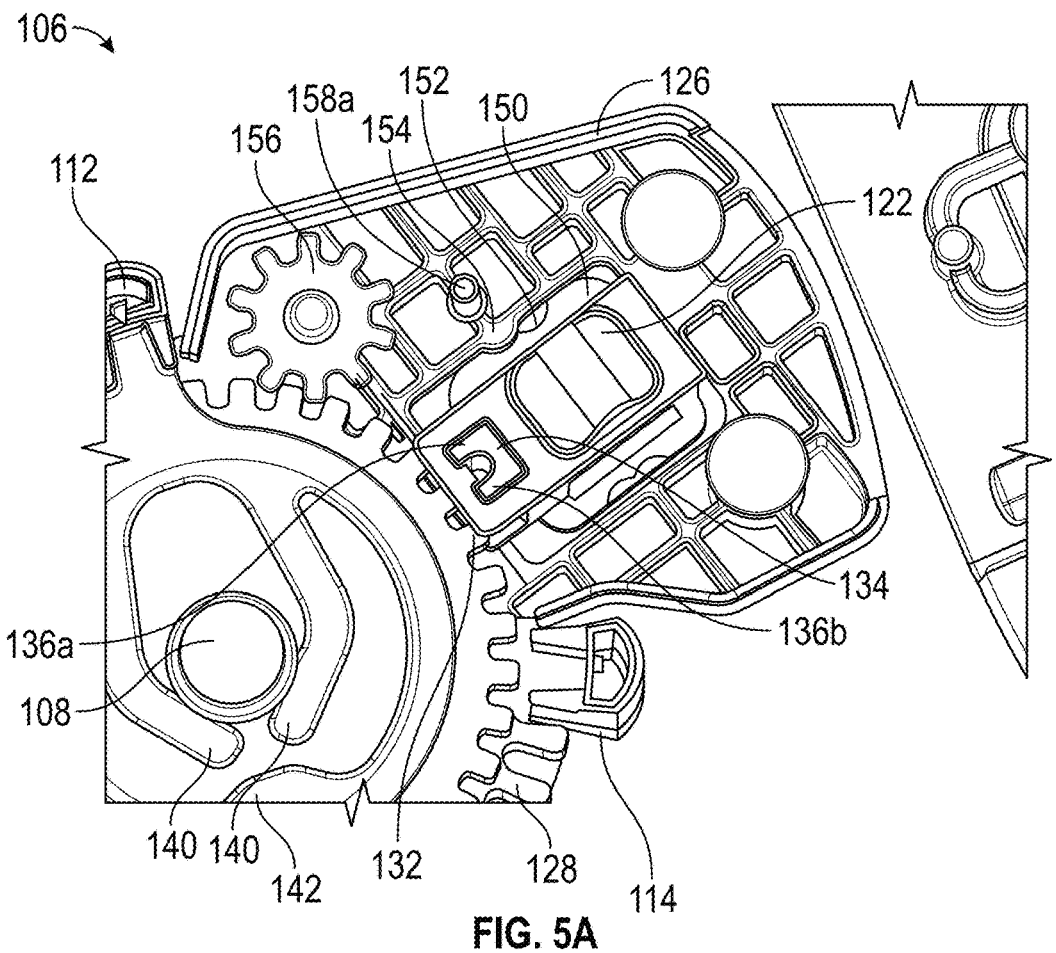
FIG. 5A illustrates a plan view of another hinge assembly of the brace of FIG. 1 in an unlocked configuration, in accordance with some embodiments.
Figure 5B:
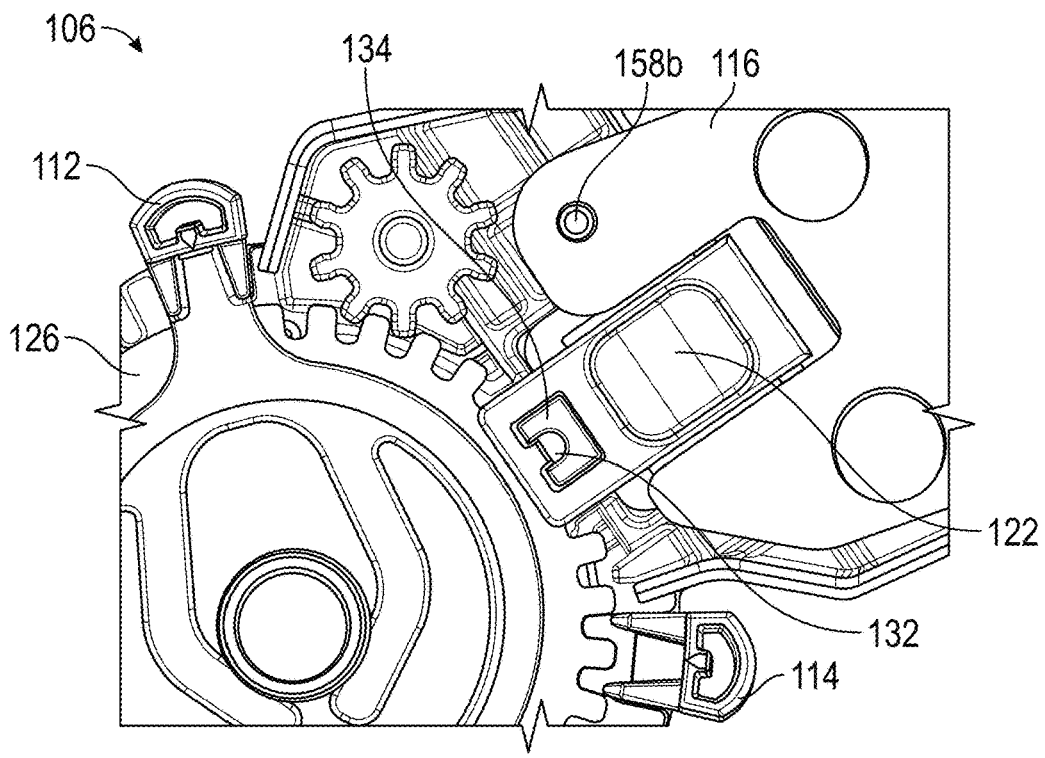
FIG. 5B illustrates a plan view of the hinge of FIG. 5A in a locked configuration.
Figure 6:
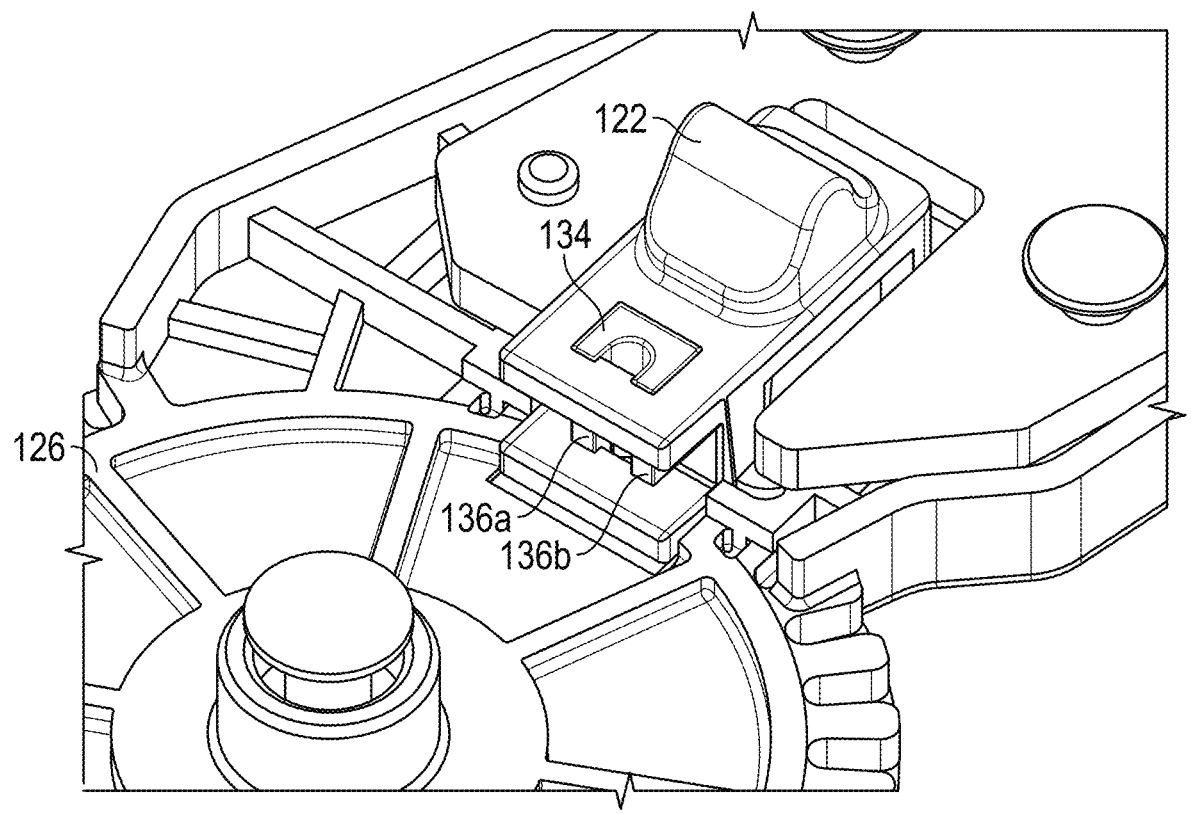
FIG. 6 illustrates a perspective view of a locking mechanism of the brace of FIG. 1, in accordance with some embodiments.

FIG. 5A illustrates a plan view of several additional features of hinge assembly 106 of brace 100 of FIG. 1 in an unlocked configuration and with outer housing 116 removed, in accordance with some embodiments, while FIG. 5B illustrates a plan view of hinge assembly 106 of FIG. 5A in a locked configuration and with outer housing 116 shown. FIGS. 5A-6 illustrate a different embodiment of the protrusions 136a and 136b. In this embodiment, the two protrusions are formed part of a single insert 134, rather than as two separate pins. In some embodiments, insert 134 comprises metal, plastic, or any other suitably rigid and inflexible material. In some other embodiments, insert 134 and first and second protrusions 136a, 136b may be formed as an integral portion of the hinge lock body itself, rather than being a separate insert.

As shown in FIG. 5A, hinge lock 122 may comprise one or more feet 150 having a plurality of recesses 152 configured to receive a protrusion 154 of upper hinge plate 126 in at least one of the locked and unlocked positions. For example, in the unlocked position shown in FIG. 5A, protrusion 154 may be disposed in a first recess of the plurality of recesses 152, which may substantially retain hinge lock 122 in the unlocked position. However, in the locked position, hinge lock 122 moves in the direction of axle 108 such that protrusion 154 is disposed in a second recess of the plurality of recesses 152, which may substantially retain hinge lock 122 in the locked position. In some embodiments, hinge lock 122 may further include, on an opposite side, another foot having a plurality of recesses configured to receive another protrusion of upper hinge plate 126, similar to that described above, may also be provided. The feet may be flexible plastic, and the open bottom of the frame allows the feet to deform inward when the hinge lock is switched between locked and unlocked positions and the protrusions 154 transition between the recesses on the feet. In addition to retaining the hinge lock in the locked or unlocked state, use of such interlocking protrusions and recesses in connection with hinge lock 122 may also provide a tactile feedback to a user that hinge lock 122 has shifted from the locked position to the unlocked position, or vice versa, even without the user having a clear view of hinge lock 122. Furthermore, this provides a simple structure, where the protrusions and recesses may be integrally formed parts of the plate and hinge lock body, rather than requiring an extra part or parts to provide this function.

Figure 7:
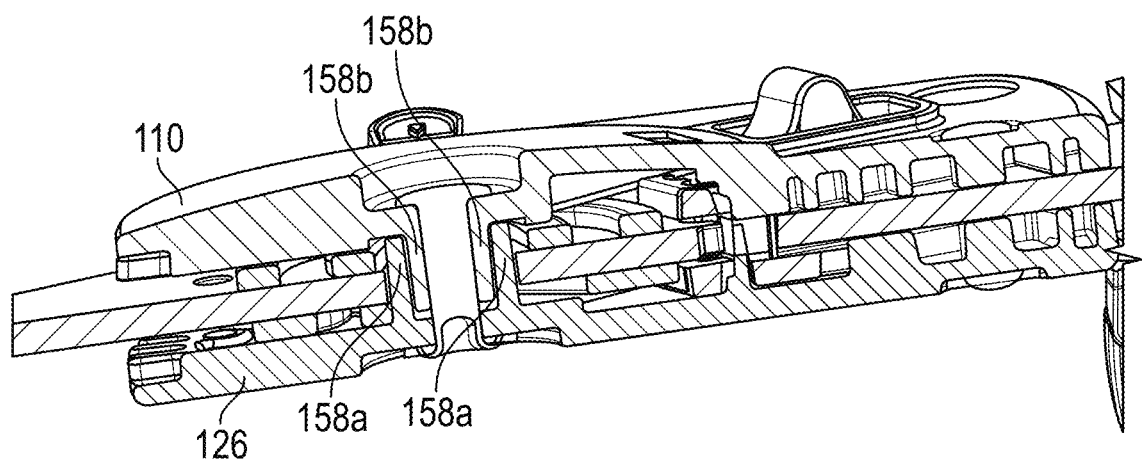
FIG. 7 illustrates a cutaway view of a hinge assembly of the brace of FIG. 1, according to some embodiments.

FIG. 7 illustrates a cutaway view of hinge assembly 106 of brace 100 of FIG. 1, according to some embodiments. As shown in FIG. 7, upper hinge plate 126 may further comprise at least a first spacing element 158a and hinge cover 110 may further comprise at least a second spacing element 158b. First and second spacing elements 158a, 158b may comprise bosses and/or may be configured to physically contact or nest within or against one another and/or against hinge cover 110 and upper hinge plate 126, respectively, when hinge cover 110 is installed on upper hinge plate 126, thereby setting a predetermined distance between hinge cover 110 and upper hinge plate 126. Utilizing spacing elements 158a, 158b allows the setting of proper spacing between hinge cover 110 and upper hinge plate 126 and thereby prevents excessive looseness or tightness of hinge assembly 106, as may otherwise occur with the use of rivets for this purpose and which could otherwise make such a brace less supportive due to such increased nominal looseness of hinge assembly 106.

Figure 8A:
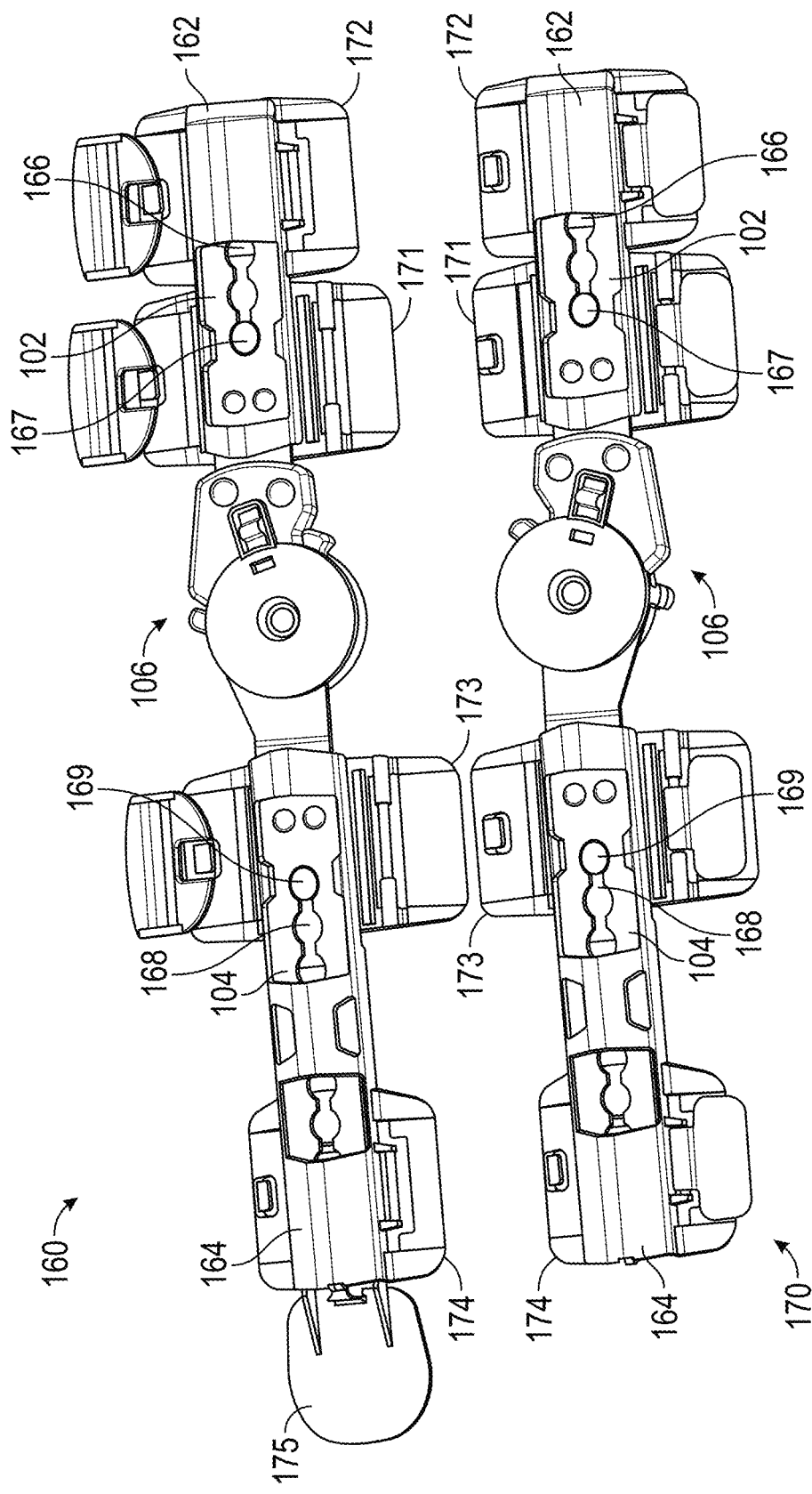
FIG. 8A illustrates a perspective view of a portion of the brace of FIG. 1, according to some embodiments.
Figure 8B:
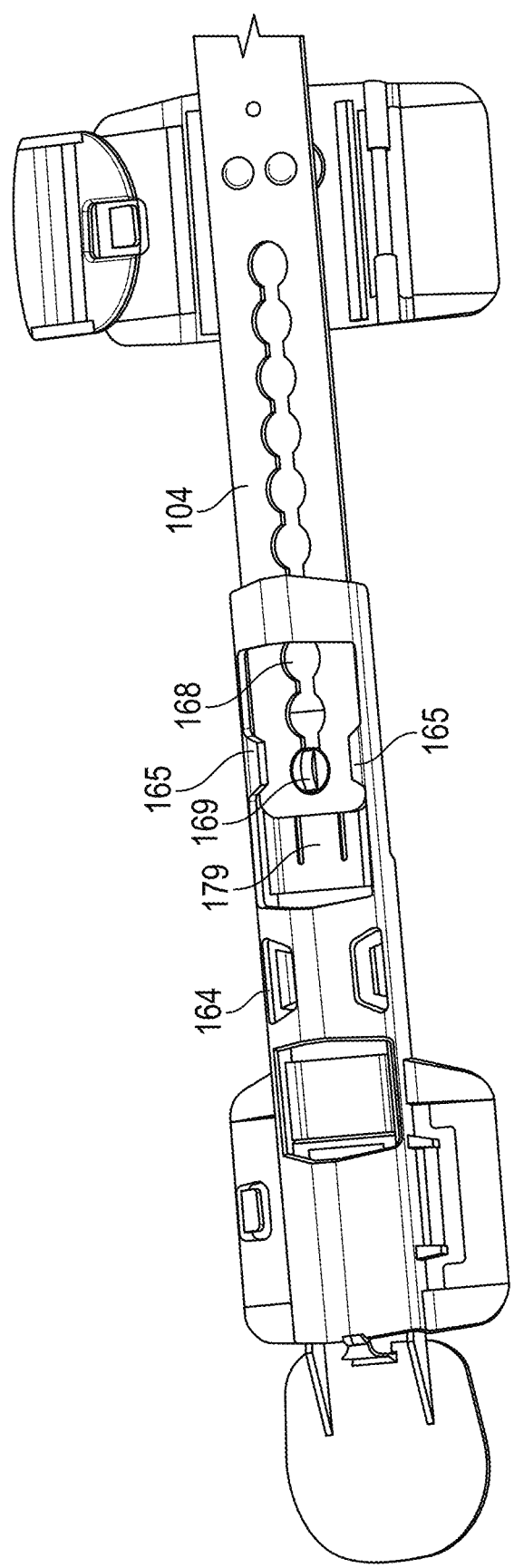
FIG. 8B illustrates a perspective view of a lower portion of the brace of FIG. 1 in a maximally extended position, according to some embodiments.

FIG. 8A illustrates a perspective view of a portion of brace 100 of FIG. 1, according to some embodiments, while FIG. 8B illustrates a perspective view of a lower portion of brace 100 in a maximally extended position, according to some embodiments. FIG. 8A illustrates lateral portion 160 of brace 100, configured to be secured against a lateral side of a user's appendage and joint, and medial portion 170 of brace 100, configured to be secured against a medial side of the user's appendage and joint. Each of lateral and medial portions 160, 170 comprise a respective upper support arm 102, lower support arm 104, and hinge assembly 106 as described in this disclosure.

Each of lateral and medial portions 160, 170 further comprises upper slider 162, configured to slidably couple to upper support arm 102 at any of a plurality of incremental degrees of extension, and lower slider 164, configured to slidably couple to lower support arm 104 at any of a plurality of incremental degrees of extension. Each of upper and lower sliders 162, 164 may be formed of any suitably rigid material, for example, plastic, which may, in some cases, be injection molded.

Upper slider 166 comprises a slider lock 167 and upper support arm 102 comprises a plurality of indexing apertures 166 configured to receive slider lock 167. Likewise, lower slider 164 comprises a slider lock 169 and lower support arm 104 comprises a plurality of indexing apertures 168 configured to receive slider lock 169. In some embodiments, slider locks 167, 169 may be integrally formed and/or molded with respective upper and lower sliders 166, 168. In some embodiments, slider locks 167, 169 may be shaped to fit and/or snap within any of the respective indexing apertures 166, 168, thereby locking upper and lower sliders 162, 164 at desired degrees of extension with respect to upper and lower support arms 102, 104. Although the general shape of slider locks 167, 169 and indexing apertures 166, 168 are illustrated as substantially circular, any other suitable shape is also contemplated. Slider locks 167, 169 are configured to deflect sufficiently to clear respective indexing apertures 166, 168 when sufficient force is applied to slider locks 167, 169 such as by pushing downward, thereby allowing sliders 162, 164 to translate freely with respect to upper and lower support arms 102, 104 during adjustment between apertures. One way of doing this is illustrated in FIG. 8B, where the slider lock 169 is molded onto a three-sided cutout 179 forming a flap in the bottom panel of the lower slider 164. Pressing down on the slider lock pushes the flap down to free the lock from the aperture and allowing the support arm to be adjusted in extension. FIGS. 8E and 8F illustrate the lower and upper sliders respectively in a fully compressed position.

Figure 9A:
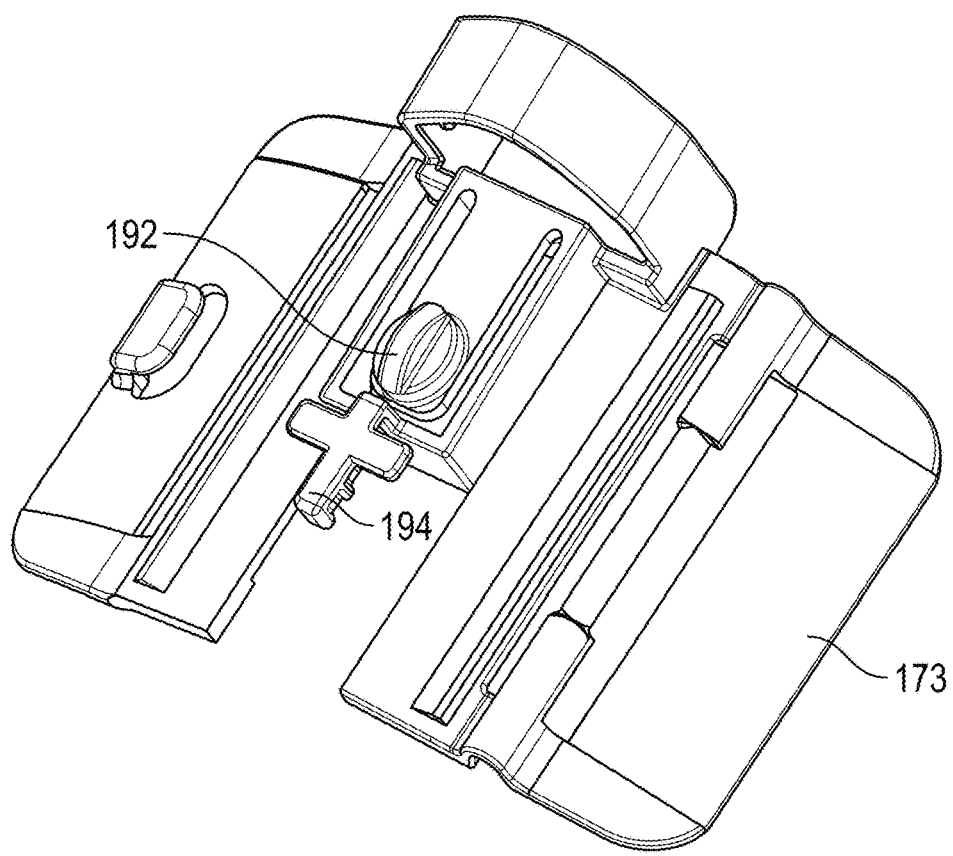
FIG. 9A illustrates an adjustable cuff for a lower support arm according to some embodiments.
Figure 9B:
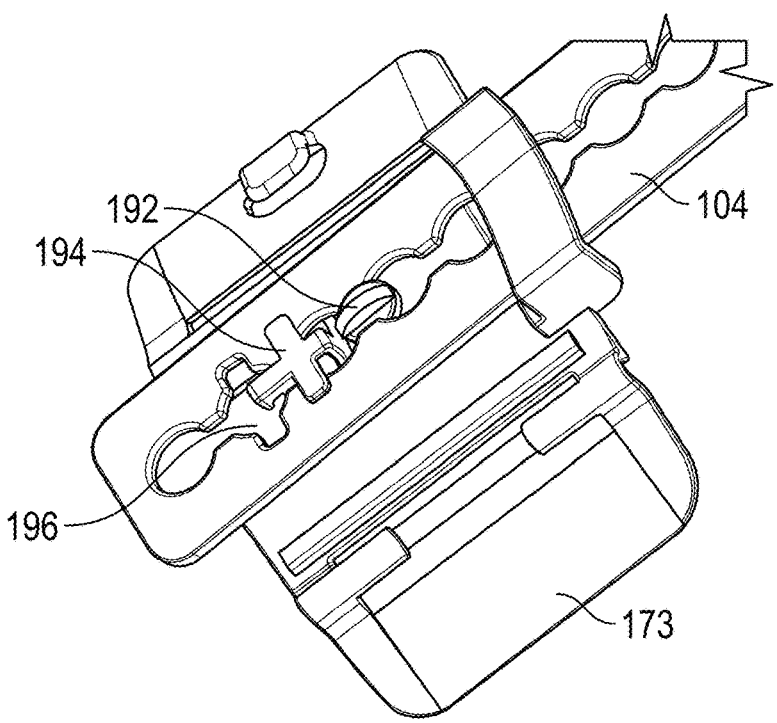
FIG. 9B illustrates the cuff of FIG. 9A being attached to the lower support arm.
Figure 9C:
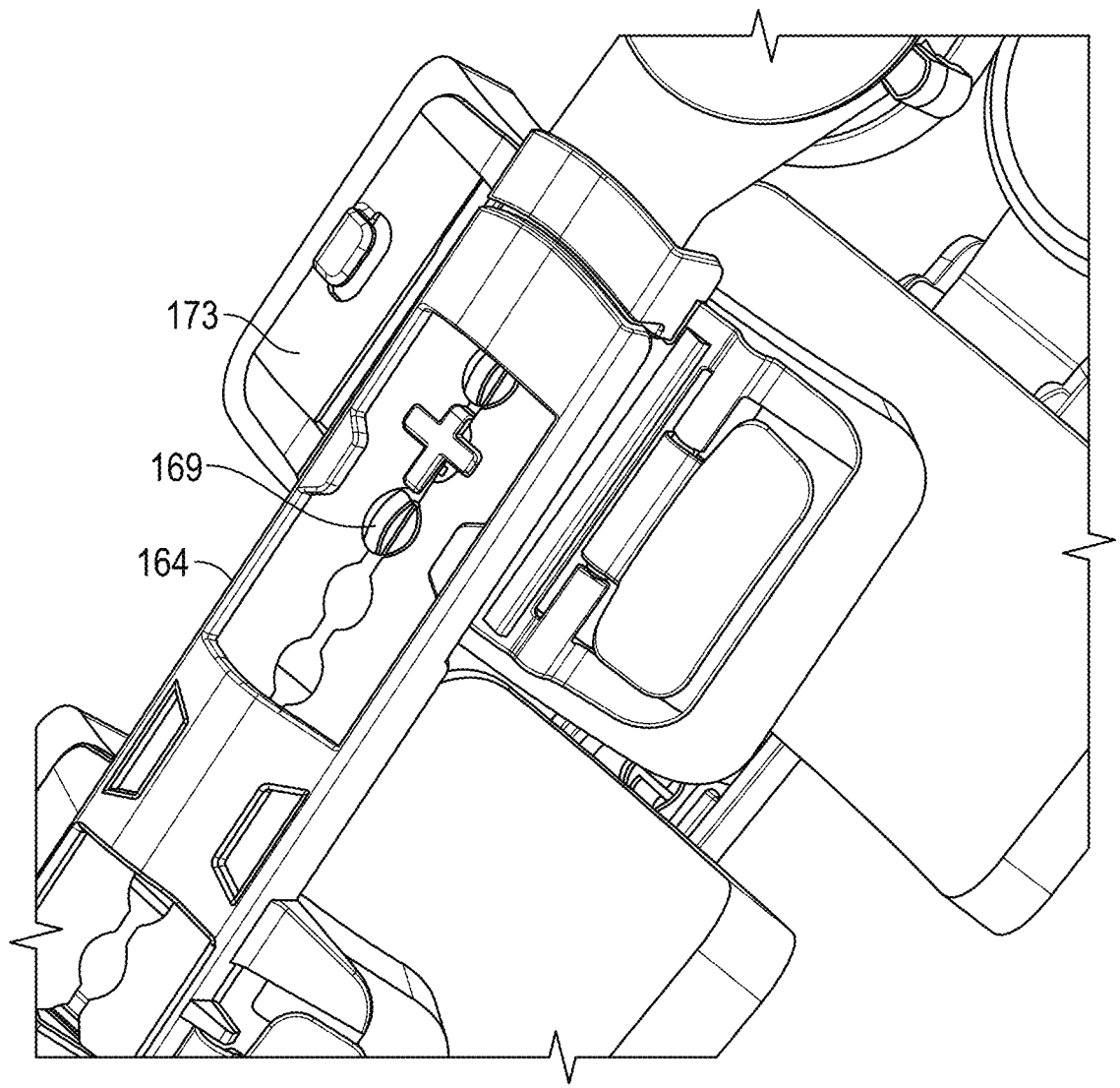
FIG. 9C illustrates a perspective view of a lower portion of the brace of FIG. 1 in a minimally extended position using the cuff of FIG. 9A, according to some embodiments.

In another implementation, rather than being riveted onto the support arms, the cuffs 171 and 173 that are next to the hinge 106 are slidably engaged with the support arms so that the distance between each cuff 171, 173 and the hinge 106 can also be adjusted. One example design of with this capability for the cuff 173 is illustrated in FIGS. 9A to 9C. Referring to FIGS. 9A and 9B, in this implementation, the cuff 173 also has a slider lock 192 attached to a three-sided cutout forming a flap (similar to the slider lock 169 illustrated in FIG. 8B). The cuff 173 also has a support arm retainer 194 molded with the body of the cuff 173. To assemble, the cuff 173 slides over the support arm 104 and up near the hinge 106. The retainer 194 passes through the slot opening 196 at the lower end of the arm 104, and then traps the cuff on the arm 104. It prevents the cuff 173 from rotating down, away from the arm 104. It also prevents rotation about the axis of the leg because it engages the slot down the center of the adjusting locations on the arm. FIG. 9C shows the cuff 173 near the hinge 106 with the lower slider 164 installed on the arm 104 below the cuff 173.

Figure 9D:
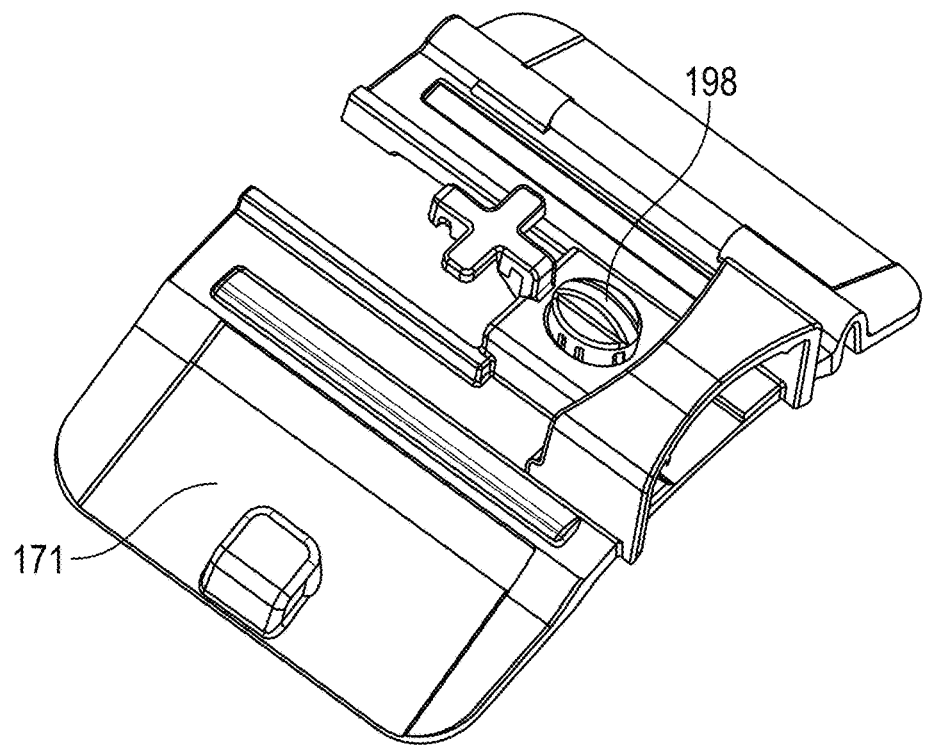
FIG. 9D illustrates an adjustable cuff for an upper support arm according to some embodiments.
Figure 9E:
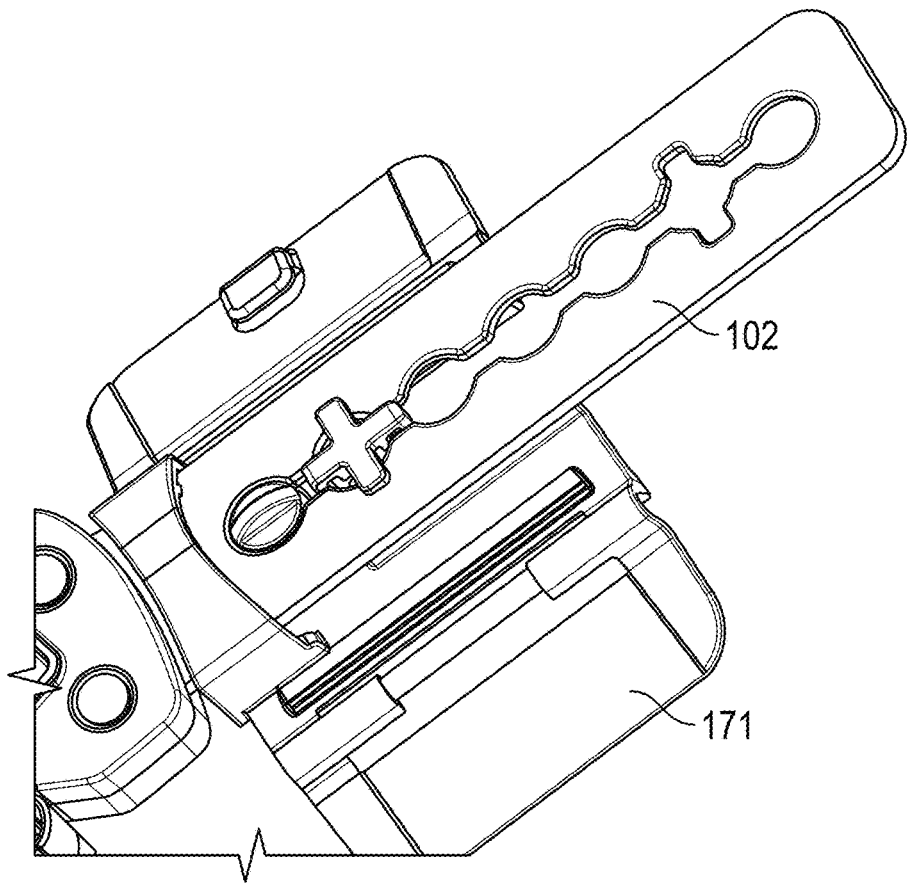
FIG. 9E illustrates the cuff of FIG. 9D attached to the upper support arm.
Figure 9F:
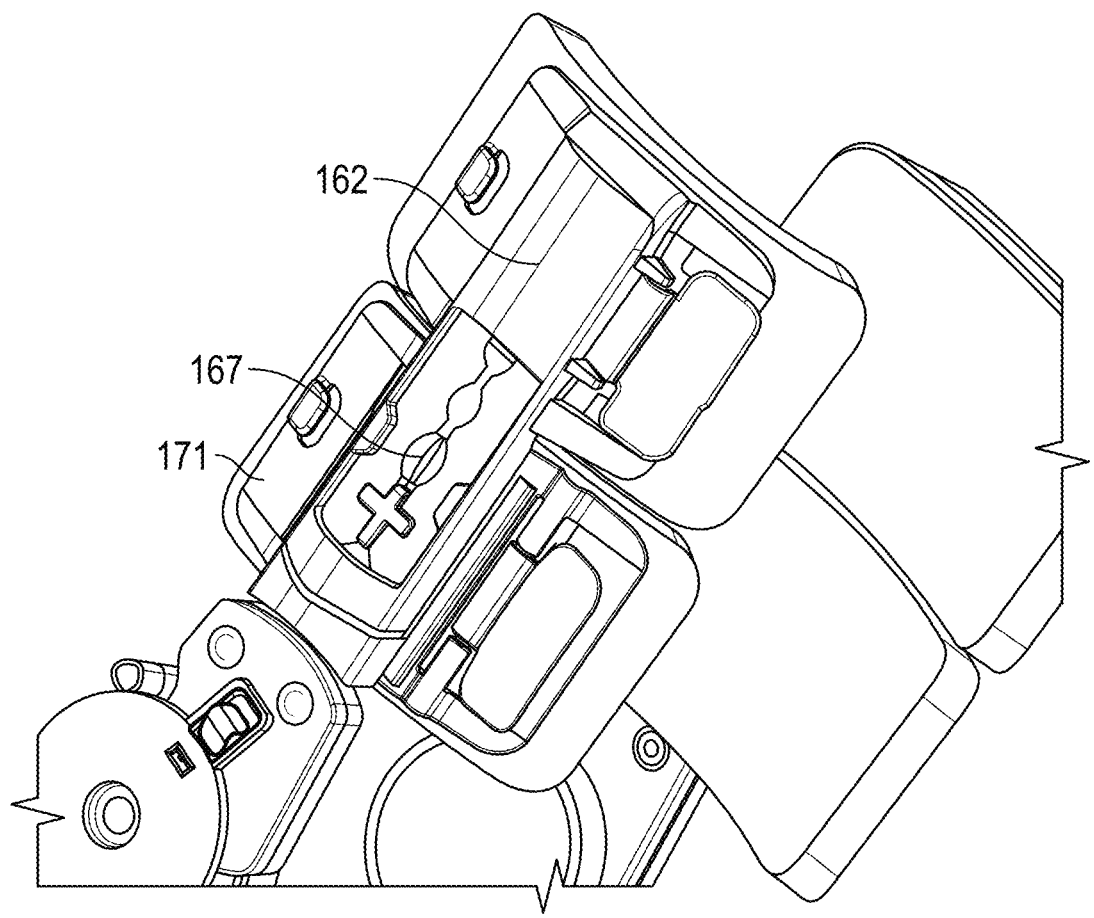
FIG. 9F illustrates a perspective view of an upper portion of the brace of FIG. 1 in a minimally extended position using the cuff of FIG. 9D, according to some embodiments.

As shown in FIGS. 9D and 9E, the upper hinge adjacent cuff 171 works the same way, but the slider lock 198 on the cuff 171 has a coil compression spring underneath, rather than being attached to a bendable flap. FIG. 9F shows the cuff 171 near the hinge 106 with the upper slider 162 installed on the arm 102 above the cuff 171.

Each of upper and lower support arms 102, 104 may further comprise indexing numerals disposed adjacent to indexing apertures 166, 168, which may facilitate easy verification that the medial and lateral sides of brace 100 are set to the same degree of extension. Moreover, because indexing apertures 166, 168 provide for discrete, rather than continuous, increments of extension, the medial and lateral sides of brace 100 may be set to the same degree of extension with greater accuracy compared to continuous adjustment designs. In addition, the indexing numerals are oriented such that they are displayed right side up when brace 100 is disposed in the proper orientation on the appendage of the user.

In addition, respective lengths and adjustments of upper and lower sliders 162, 164 and upper and lower support arms 102, 104 are such that a broader range of persons (e.g., taller and/or shorter persons) may be accommodated by brace 100 compared to other braces. For example, upper support arm 102 may comprise a first number of indexing apertures 166 (e.g., 3), while lower support arm 104 may comprise a second number of indexing apertures 168 (e.g., 10).

In some embodiments, each lower slider 164 further comprises a pair of tabs 165 integrally formed and/or molded with lower slider 164 and configured to contact lower support arm 104 at least when lower slider 164 is at its greatest degree of extension with respect to lower support arm 104, thereby greatly reducing an amount of looseness between lower support arm 104 and lower slider 164 at this greatest degree of extension. Since tabs 165 are integrally formed and/or molded with lower slider 164, tabs 165 provide a passive tightening feature that does not require additional parts, thereby decreasing cost and complication associated with manufacturing and/or assembly of brace 100.

In addition, each of upper and lower sliders 162, 164 may be designed for injection molding such that their molding doesn't require any side action in the tooling. For example, all side edges of upper and lower sliders 162, 164 may be substantially perpendicular to a plane of upper and lower sliders 162, 164, or may slope to one side or the other of perpendicular (but not both at any given point on the sides), so that side molds are not required to allow clearance of lower sliders 162, 164 from their injection molds. In further example, where a portion of upper and lower sliders 162, 164 contact or extend over a respective portion of one side of upper and lower support arms 102, 104, upper and lower sliders 162, 164 do not contact or extend over that same portion on the opposite side of upper and lower support arms 102, 104. Such a deliberate design not only reduces tool cost and complexity, it also lowers part cost through faster manufacture cycle time compared to other designs in which side action in the tooling is required to remove a part from its injection mold.

Brace 100 may further comprise a removable malleoli attachment 175 configured to removably snap into a distal end of lower slider 164. Removable malleoli attachment 175 is configured to abut a distal portion of the user's appendage (e.g., an ankle) when brace 100 is worn, thereby preventing or substantially reducing migration of brace 100. A user may selectively attach or remove removable malleoli attachment 175 from either or both lower sliders 164, thereby enjoying the increased flexibility compared to braces that either do not include malleoli attachments or that provide permanent malleoli features.

Each of lateral and medial portions 160, 170 of brace 100 may further comprise a first cuff 171, a second cuff 172, a third cuff 173 and a fourth cuff 174, each configured to receive a respective strap for securing brace 100 to the appendage of the user at various locations above and below the joint of the user. First and third cuffs 171, 173 may be disposed proximal to and respectively above and below hinge assembly 106 and the joint of the user, while second and fourth cuffs 172, 174 may be disposed distal to and respectively above and below hinge assembly 106 and the joint of the user. First cuff 171 may be coupled to upper support arm 102, while second cuff 172 may be coupled to or, alternatively, integrally formed and/or molded with upper slider 162. Likewise, third cuff 173 may be coupled to lower support arm 104, while fourth cuff 174 may be coupled to or, alternatively, integrally formed and/or molded with lower slider 164. First, second, third and fourth cuffs 171-174 may be formed of any suitably rigid material, e.g., metal, plastic, fiberglass composite, etc.

Figure 8C:
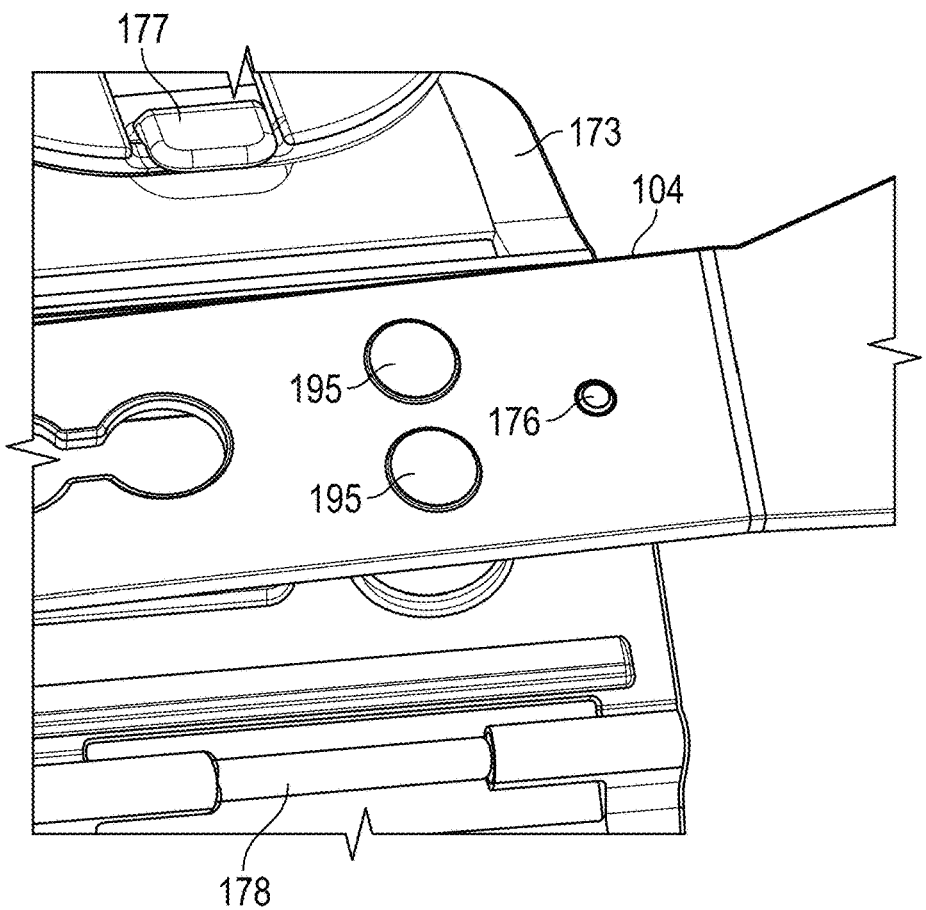
FIG. 8C illustrates a perspective view of attachment of a cuff to a support arm according to some embodiments.
Figure 8D:
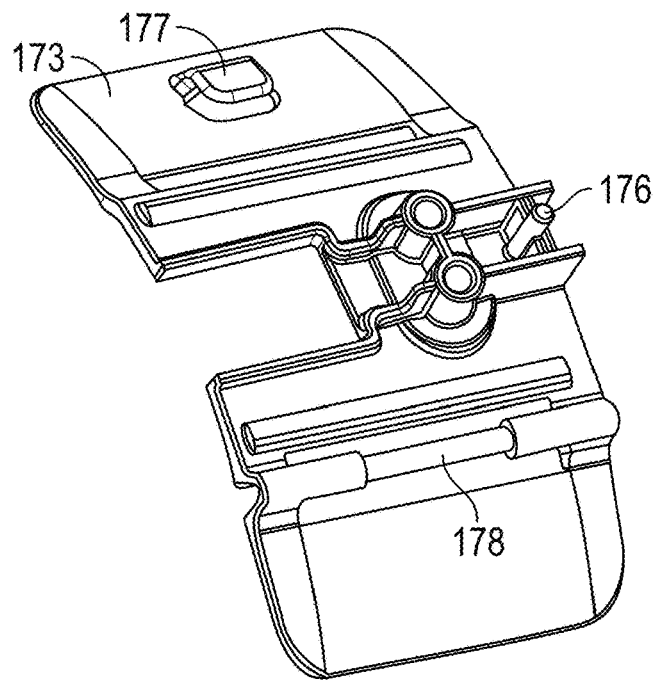
FIG. 8D illustrates the cuff of FIG. 8C separated from the support arm.
Figure 8E:
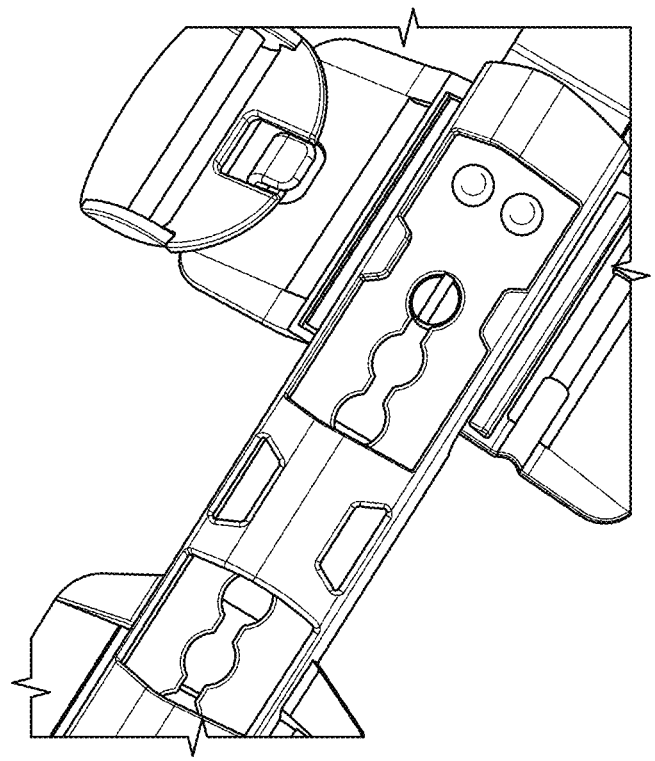
FIG. 8E illustrates a perspective view of a lower portion of the brace of FIG. 1 in a minimally extended position, according to some embodiments.
Figure 8F:
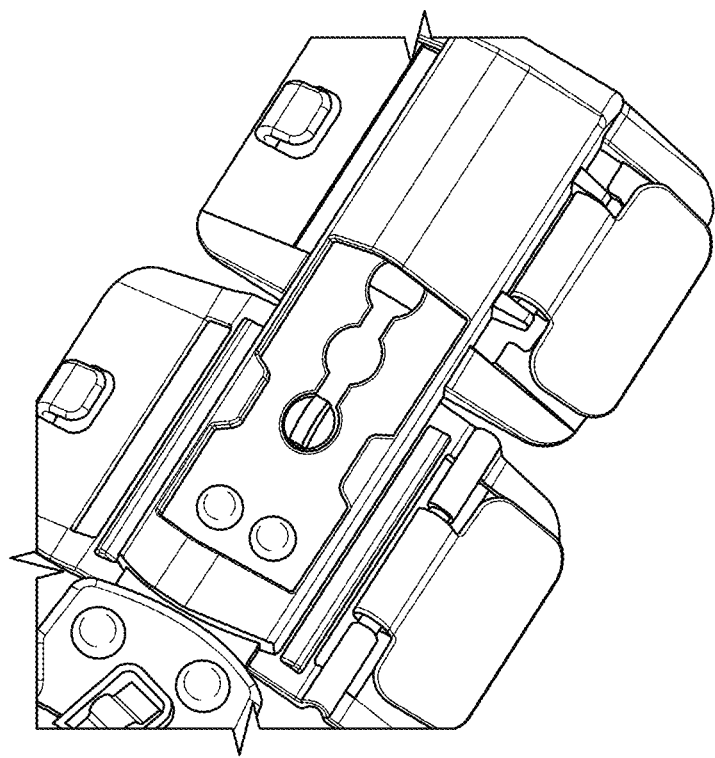
FIG. 8F illustrates a perspective view of an upper portion of the brace of FIG. 1 in a minimally extended position, according to some embodiments.

FIG. 8C illustrates a magnified perspective view of a portion of third cuff 173 coupled to lower support arm 104, according to some embodiments, while FIG. 8D illustrates a perspective view of third cuff 173 separate and apart from lower support arm 104 for ease of viewing. Third cuff 173 comprises a first fixing element 177 disposed on one side of third cuff 172 and configured to receive a buckle for securing a strap of brace 100. In some embodiments, first fixing element 177 comprises a hook. Third cuff 173 comprises a second fixing element 178 disposed on an opposite side of third cuff 172 and configured to receive a strap retaining element, for example a cam and/or flap comprising a hook-and-loop, snap, or any other suitable fastening material on its underside configured to attach to and immobilize the strap. In some embodiments, such a cam and/or flap has an increased resistance to rotation when raised to prevent it from prematurely contacting the strap and thereby undesirably impeding strap adjustment, and a reduced resistance to rotation when partially lowered to facilitate contact between the cam and/or flap and the strap. In some embodiments, second fixing element 178 comprises a bar or shaft. Third cuff 173 further comprises a round boss or protrusion 176 configured to extend through a mating aperture in lower support arm 104, thereby aligning third cuff 173 for attachment with rivets 195 to lower support arm 104 without a need for an added fixture for such alignment during manufacture.

First cuff 171 may have substantially similar form and construction to third cuff 173, however, protrusion 176 being configured to extend through a mating aperture in upper support arm 102 rather than lower support arm 104. Second and fourth cuffs 172, 174 may have substantially similar form and construction to third cuff 173 with respect to at least first and second fixing elements 177, 178.

Figure 10:
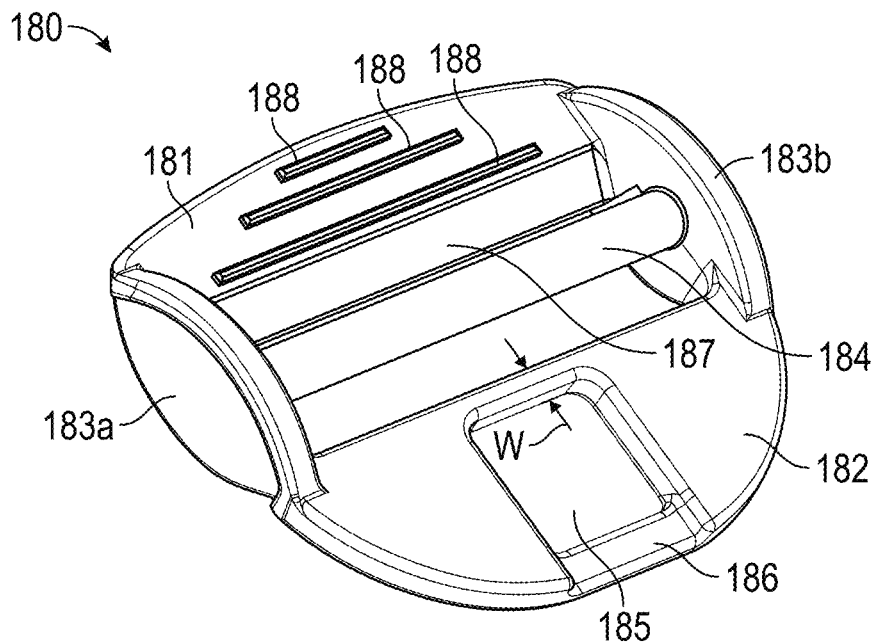
FIG. 10 illustrates a perspective view of a buckle for use with the brace of FIG. 1, according to some embodiments.

FIG. 10 illustrates a perspective view of a buckle 180 for use with brace 100, according to some embodiments. As will be described in more detail below, several aspects of buckle 180 provide improved resistance to unintended strap loosening and allow better conformance to at least a portion of an appendage of the user, thereby preventing or substantially reducing brace migration when brace 100 is worn by the user. Buckle 180 may be formed of any suitably rigid material, e.g., metal, plastic, fiberglass composite, etc.

Buckle 180 comprises a first portion 181 and a second portion 182 separated from one another by a space and coupled to one another at their outer edges via first and second bridging elements 183a, 183b. In some embodiments, an upper surface of first and second portions 181, 182 may be substantially planar. In other embodiments, the upper surface of one or both of first and second portions 181, 182 may have a slight convex curvature (when viewed from the outside) in at least one dimension. In this way, a strap may pass over the upper surfaces of first and second portions 181, 182.

In some embodiments, first and second bridging elements 183a, 183b may have a substantially elliptical or football-shaped cross-section, perpendicular to the upper surfaces of first and second portions 181, 182, such that first and second bridging elements 183a, 183b bow outward toward their middles with respect to their direction of extension. In this way, first and second bridging elements 183a, 183b may limit lateral strap movement within buckle 180.

Buckle 180 further comprises a shaft 184 extending between first and second bridging elements 183a, 183b in the space between facing edges of first and second portions 181, 182. Shaft 184 may be substantially cylindrical, having a longitudinal axis extending substantially parallel to an upper surface of at least one of first portion 181 and second portion 182, and substantially perpendicular to facing surfaces of first and second bridging elements 183a, 183b. Shaft 184 may be disposed such that its longitudinal axis lies substantially in, or slightly below, a plane of the upper surface of at least one of first portion 181 and second portion 182. At least a portion of shaft 184 is configured to contact a strap passing through buckle 180.

First portion 181 may further have a beveled edge 187 facing second portion 182 configured to direct the strap as it passes through buckle 180. First portion 181 may further comprise one or more ridges 188 on its upper surface configured to provide increased resistance to strap movement when brace 100 is worn.

Second portion 182 comprises an aperture 185 configured to receive a hook of any of first, second, third or fourth cuffs 171-174. Second portion 182 further comprises a recessed portion 186 having a reduced thickness adjacent to aperture 185. Recessed portion 186 is configured to abut at least a portion of the hook of any of first, second, third or fourth cuffs 171-174, thereby restraining lateral movement of buckle 180 when coupled to any of cuffs 171-174. A segment of second portion 182, having width "W," separating an inner edge of second portion 182 and an adjacent edge of aperture 185 is designed to be as narrow as practical, thereby reducing a total length of buckle 180. Such a reduced total length of buckle 180 allows buckle 180 to more closely conform to a narrow portion of the appendage of the user (e.g., the ankle) compared to buckles having longer total lengths, which further prevents or substantially reduces brace migration when brace 100 is worn by facilitating a closer fit with the appendage. In some embodiments, while inner, facing edges of first and second portions 181, 182 may be substantially parallel to each other, opposing, outer edges of first and second portions 181, 182 may be substantially curved.

Figure 11:
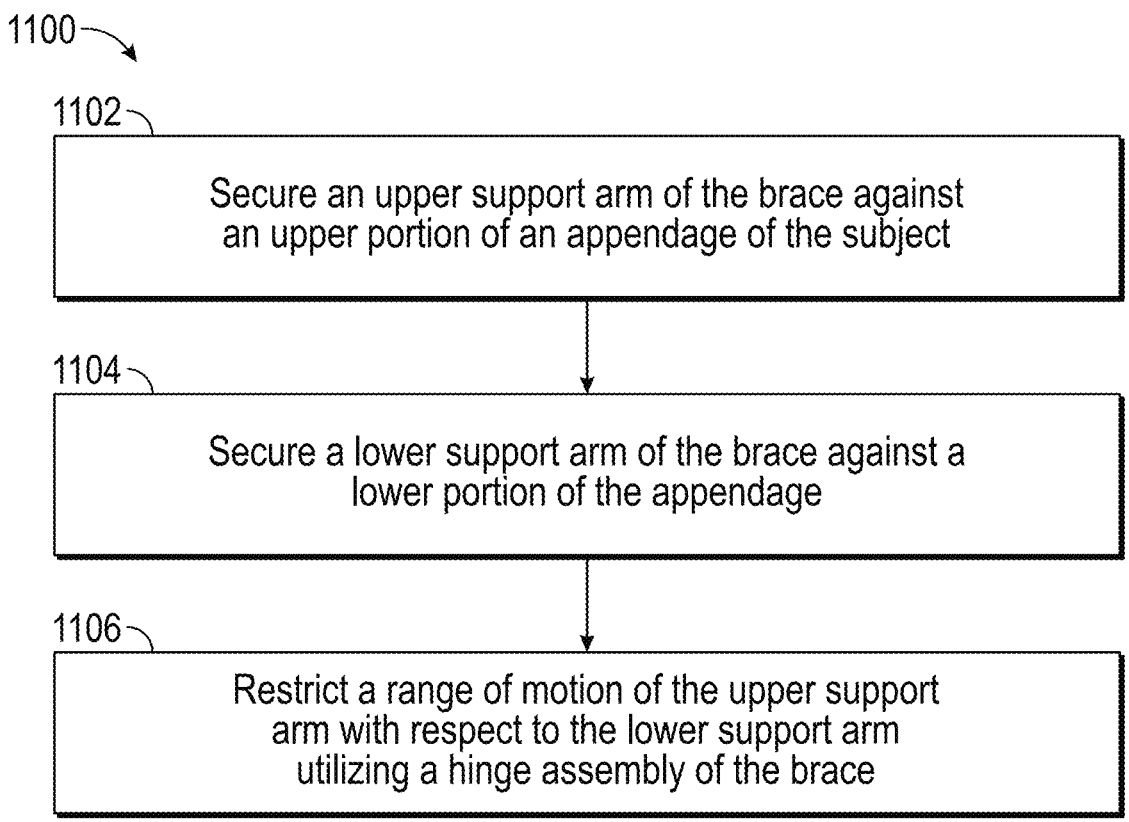
FIG. 11 illustrates a flowchart of a method a method of using a brace configured for attachment to a joint of a subject, in accordance with some embodiments.

FIG. 11 illustrates a flowchart 1100 of a method of restricting a range of motion of a joint of a subject utilizing a brace configured for attachment to the joint, in accordance with some embodiments. Flowchart 1100 may apply to the utilization of any brace described in this disclosure. While certain blocks are described, flowchart 1100 may include more, fewer or different blocks, steps and/or actions from those described, and/or in the same or a different order than described.

Block 1102 includes securing an upper support arm of the brace against an upper portion of an appendage of the subject. For example, as previously described, upper support arm 102 may be secured to an upper portion of an appendage (e.g., a thigh) of a user via one or more straps, in some cases, utilizing first cuff 171.

Block 1104 includes securing a lower support arm of the brace against a lower portion of the appendage. For example, as previously described, lower support arm 104 may be secured to a lower portion of an appendage (e.g., a lower leg) of a user via one or more straps, in some cases, utilizing third cuff 173.

Block 1106 includes restricting a range of motion of the upper support arm with respect to the lower support arm utilizing a hinge assembly of the brace. For example, as previously described, hinge assembly 106 comprises upper hinge plate 126 coupled to upper support arm 102, lower hinge plate 130 coupled to lower support arm 104, and axle 108 rotatably coupling upper hinge plate 126 and lower hinge plate 130. Upper hinge plate 126 comprises a first plurality of teeth 128 disposed along at least a portion of a perimeter of upper hinge plate 126, while lower hinge plate 130 comprises a second plurality of teeth 132 disposed along at least a portion of a perimeter of lower hinge plate 130. Hinge assembly 106 further comprises a locking element 122 disposed on upper hinge plate 126, locking element 122 comprising first protrusion 136a and second protrusion 136b configured to physically contact opposite sides of one of second plurality of teeth 132 in a first orientation, thereby prohibiting rotation of upper support arm 102 with respect to lower support arm 104.

Figure 12:
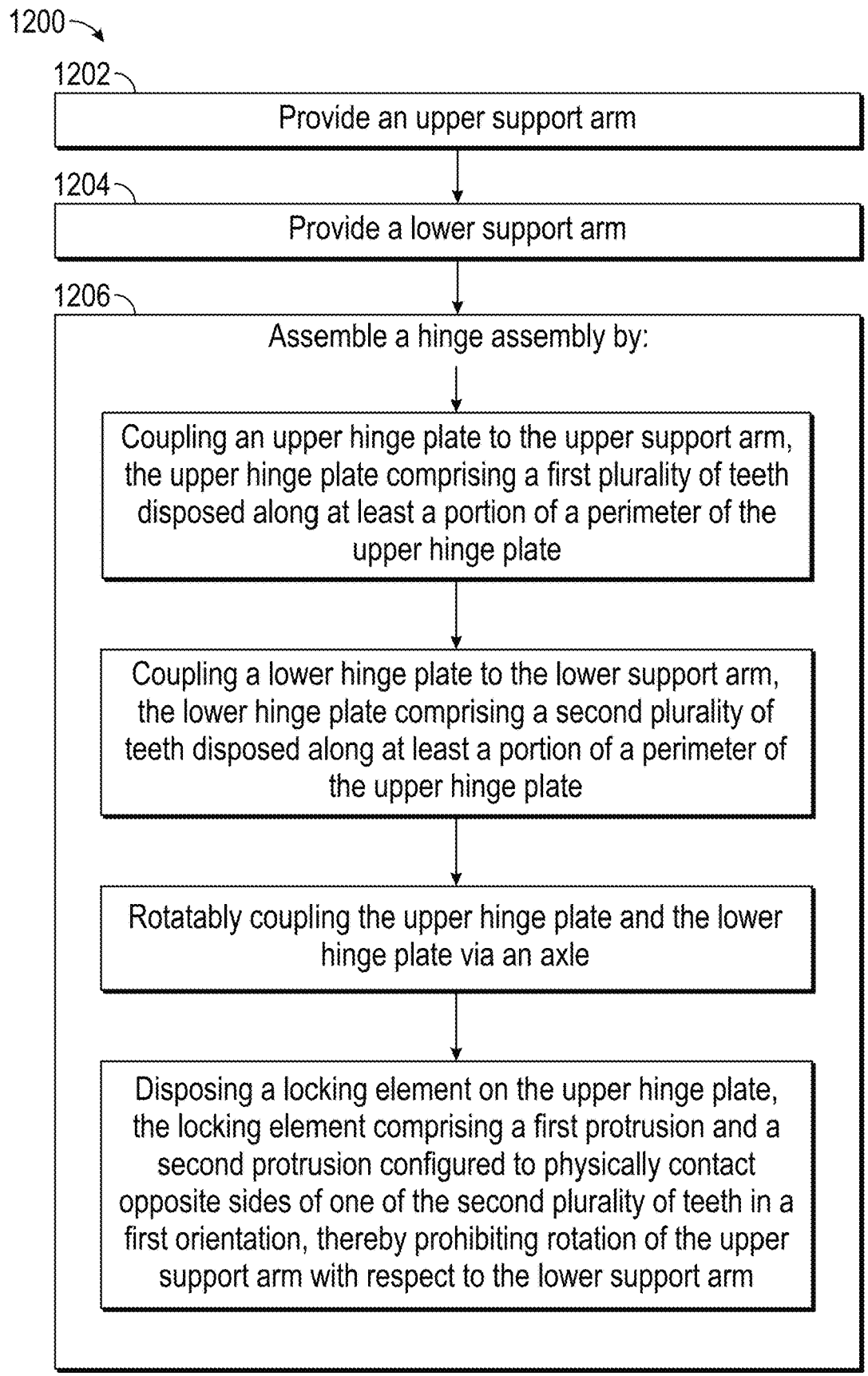
FIG. 12 illustrates a flowchart of a method of a method of manufacturing a brace configured for attachment to a joint of a subject, in accordance with some embodiments.

FIG. 12 illustrates a flowchart 1200 of a method of manufacturing a brace configured to restrict a range of motion of a joint of a subject, in accordance with some embodiments. Flowchart 1200 may apply to the manufacture of any brace described in this disclosure. While certain blocks are described, flowchart 1200 may include more, fewer or different blocks, steps and/or actions from those described, and/or in the same or a different order than described.

Block 1202 includes providing an upper support arm. For example, providing upper support arm 102 may comprise receiving and making available, forming, molding or stamping upper support arm 102, which may be formed of any suitably rigid material, e.g., metal, plastic, fiberglass composite, etc.

Block 1204 includes providing a lower support arm. For example, providing lower support arm 104 may comprise receiving and making available, forming, molding or stamping lower support arm 104, which may be formed of any suitably rigid material, e.g., metal, plastic, fiberglass composite, etc.

Block 1206 includes assembling a hinge assembly. For example, assembling hinge assembly 106 may include coupling upper hinge plate 126 to upper support arm 102 utilizing any suitable coupling element(s), for example rivets, screws or welds. Upper hinge plate 126 includes a first plurality of teeth 128 disposed along at least a portion of a perimeter of upper hinge plate 126. Assembling hinge assembly 106 may further include coupling lower hinge plate 130 to lower support arm 104 utilizing any suitable coupling element(s), for example rivets, screws or welds. Lower hinge plate 130 includes a second plurality of teeth 132 disposed along at least a portion of a perimeter of upper hinge plate 130. Assembling hinge assembly 106 may further include rotatably coupling upper hinge plate 126 and lower hinge plate 130 via axle 108. Assembling hinge assembly 106 may further include disposing locking element 122 on upper hinge plate 126. Locking element 122 includes first protrusion 136a and second protrusion 136b configured to physically contact opposite sides of one of the second plurality of teeth 132 in a first orientation, thereby prohibiting rotation of upper support arm 102 with respect to lower support arm 104.

Although the present disclosure has been described in terms of certain preferred features, other features of the disclosure including variations in dimensions, configuration and materials will be apparent to those of skill in the art in view of the disclosure herein. In addition, all features detailed in connection with any one aspect herein can be readily adapted for use in other aspects herein. The use of different terms or reference numerals for similar features in different embodiments does not imply differences other than those which may be expressly set forth. Accordingly, the present disclosure is intended to be described solely by reference to the appended claims, and not limited to the preferred embodiments disclosed herein.

What is claimed is:

1. A brace configured to restrict a range of motion of a joint of a subject, the brace comprising:
   an upper support arm;
   a lower support arm;
   a hinge assembly configured to rotatably couple the upper support arm to the lower support arm;
   a plurality of cuffs, each coupled directly or indirectly to the upper support arm or the lower support arm and configured to receive a respective strap for securing the brace to an appendage of the subject;
   a plurality of buckles, each configured to be coupled to a respective one of the plurality of cuffs and to receive one of the respective straps;
   an upper slider configured to slidably couple to the upper support arm at any of a first plurality of incremental amounts of extension; and
   a lower slider configured to slidably couple to the lower support arm at any of a second plurality of incremental amounts of extension, wherein:
   the lower slider comprises a slider lock, and
   the lower support arm comprises a plurality of indexing apertures disposed along a slot configured to receive the slide lock, wherein the slider lock is configured to deflect sufficiently to clear the plurality of indexing apertures when sufficient force is applied to the slider lock, thereby allowing the lower slider to translate freely within the slot and with respect to the lower support arm during adjustment between apertures.

2. The brace of claim 1, wherein each of the plurality of buckles comprises:
   a first planar portion;
   a second planar portion separated from the first planar portion by a space;
   a first bridging element disposed perpendicular to the first and second planar portions and coupling a first outer edge of the first planar portion to a first outer edge of the second planar portion; and
   a second bridging element disposed perpendicular to the first and second planar portions and coupling an opposing second outer edge of the first planar portion to an opposing second outer edge of the second planar portion.

3. The brace of claim 2, wherein each of the plurality of cuffs comprises a respective hook and wherein the second planar portion of each of the plurality of buckles comprises an aperture configured to receive any one of the respective hooks and, thereby, secure the respective buckle to the respective cuff.

4. The brace of claim 3, wherein the second planar portion of each of the plurality of buckles comprises a segment, separating an edge of the second planar portion abutting the space and an adjacent edge of the aperture, having a sufficiently small extent to allow the buckle to conform to a contour of an ankle of the subject.

5. The brace of claim 4, wherein at least one of the plurality of cuffs comprises a strap retaining element comprising a rotatable cam or a flap having a hook and loop fastener configured to attach to and immobilize the respective strap.

6. The brace of claim 3, wherein the aperture has a square or rectangular form factor with rounded corners.

7. The brace of claim 3, wherein the second planar portion of each of the plurality of buckles comprises a recessed portion adjacent to the aperture, the recessed portion having a reduced thickness compared to immediately adjacent portions of the second planar portion and being configured to abut at least a portion of the respective hook of any of the plurality of cuffs and, thereby, restrain lateral movement of the buckle when coupled to any of the plurality of cuffs.

8. The brace of claim 2, wherein the first bridging element and the second bridging element each have an elliptical or football-shaped cross-section perpendicular to upper surfaces of the first and second planar portions, such that a middle of each of the first bridging element and the second bridging element bows outward perpendicularly to the upper surfaces of the first and second planar portions, thereby limiting lateral movement of the respective strap within the buckle.

9. The brace of claim 8, wherein the upper surface of the first planar portion comprises a plurality of ridges configured to provide increased resistance to movement of the respective strap when the brace is secured to the appendage of the subject.

10. The brace of claim 2, wherein the buckle further comprises a shaft extending between the first and second bridging elements in the space between the first and second portions, a longitudinal axis of extension of the shaft being parallel to an upper surface of at least one of the first planar portion and the second planar portion and perpendicular to facing surfaces of the first and second bridging elements.

11. The brace of claim 10, wherein the longitudinal axis of extension of the shaft is in a plane below a plane of the upper surface of at least one of the first planar portion and the second planar portion.

12. The brace of claim 2, wherein the first planar portion comprises a beveled edge facing the second planar portion and configured to direct the respective strap within the buckle.

13. The brace of claim 2, wherein facing edges of the first and second planar portions are parallel.

14. The brace of claim 2, wherein opposing outer edges of the first and second planar portions are curved.

15. The brace of claim 1, wherein the lower slider comprises at least one tab integrally formed with the lower slider and configured to contact the lower support arm at least when the lower slider is disposed at a greatest amount of extension with respect to the lower support arm.

16. The brace of claim 15, wherein the at least one tab is integrally formed or molded with the lower slider.

* * * * *